(12) United States Patent
Khosla et al.

(10) Patent No.: US 7,462,688 B2
(45) Date of Patent: Dec. 9, 2008

(54) PEPTIDES FOR DIAGNOSTIC AND THERAPEUTIC METHODS FOR CELIAC SPRUE

(75) Inventors: Chaitan Khosla, Palo Alto, CA (US); Jiang Xia, Stanford, CA (US); Matthew John Siegel, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 177 days.

(21) Appl. No.: 11/198,068

(22) Filed: Aug. 4, 2005

(65) Prior Publication Data

US 2006/0189540 A1 Aug. 24, 2006

Related U.S. Application Data

(63) Continuation-in-part of application No. 10/514,005, filed as application No. PCT/US03/15506 on May 14, 2003, said application No. 11/198,068 is a continuation-in-part of application No. 10/531,547, filed as application No. PCT/US03/37434 on Nov. 20, 2003.

(60) Provisional application No. 60/380,761, filed on May 14, 2002, provisional application No. 60/392,782, filed on Jun. 28, 2002, provisional application No. 60/422,933, filed on Oct. 31, 2002, provisional application No. 60/428,033, filed on Oct. 20, 2002.

(51) Int. Cl.
*A61K 38/00* (2006.01)
*A61K 51/00* (2006.01)

(52) U.S. Cl. ......................... 530/326; 514/15; 424/1.69

(58) Field of Classification Search .................... 514/15
See application file for complete search history.

(56) References Cited

U.S. PATENT DOCUMENTS

| 5,834,428 | A | 11/1998 | Drucker |
| 6,197,356 | B1 | 3/2001 | Girsh |
| 6,319,726 | B1 | 11/2001 | Schuppan |
| 6,410,550 | B1 | 6/2002 | Coe |
| 2001/0036639 | A1 | 11/2001 | Fine |
| 2002/0215438 | | 11/2003 | Hausch |
| 2004/0241664 | A1 | 12/2004 | Dekker et al. |

FOREIGN PATENT DOCUMENTS

| EP | 0 905 518 A1 | 3/1999 |
| WO | WO 94/26774 | 11/1994 |
| WO | WO 01/25793 A2 | 4/2001 |
| WO | WO 03/068170 | 8/2003 |

OTHER PUBLICATIONS

Ahnen et al., Intestinal Aminooligopeptidase. In Vivo Synthesis on Intracellular Membranes of Rat Jejunum, 1982, J. Biol. Chem., 257, 12129-35.
Arentz-Hansen et al., The Intestinal T Cell Response to α—Gliadin in Adult Celiac Disease is Focused on a Single Deamidated Glutamine Targeted by Tissue Transglutaminase, 2000, J. Exp. Med., 191, 603-12.
Bordusa et al., The Specidicity of Prolyl Endopeptidase from Flavobacterium Meningoseptum: Mapping the S' Subsites by Positional Scanning Via Acyl Transfer,1998, Bioorg. Med. Chem., 6, 1775-80.
Colot et al., The Genes Encoding Wheat Storage Proteins: Towards a Molecular Understanding of Bread-Making Quality and its Genetic Manipulation, 1990, Genet Eng,, 12:225-41.
Database Derwent, Acc-No 1996-329479, HLA-Binding Oligopeptide and an Immuno: Regulator Contgit—Used in the Treatment of Auto: Immune Disease, 1999.
Lahteenoja et al., Local Challenge on Oral Mucosa With an Alpha-Gliadin Related Synthetic Peptide in Patients With Celica Disease, 2000, Am. J. Gastroenterol., 95: 2880.
Schuppan, Current Concepts of Celiac Disease Pathogenesis, 2000, Gastroenterology, 119, 234-42.
Wieser, The Precipitating Factor in Coelica Disease, 1995, Baillieres Clin Gastroenterol, 9(2):191-207.
Wieser, 1996, Relation Between Structure an Dcoeliac Toxicity, Acta Paediatr Suppl., 412:3-9.
Yoshimoto et al., Prolyll Endopeptidase From Flavobacterium Meningosepticum: Cloning and Sequencing of the Enzyme Gene, 1991, J. Biochem., 110, 873-8.

*Primary Examiner*—Cecilia Tsang
*Assistant Examiner*—Maury Audet
(74) *Attorney, Agent, or Firm*—Bozicevic, Field & Francis LLP; Pamela J. Sherwood

(57) ABSTRACT

Detection of toxic gluten oligopeptides refractory to digestion and antibodies and T cells responsive thereto can be used to diagnose Celiac Sprue. Analogs of such oligopeptides are useful in the inhibition of immune responses.

7 Claims, 15 Drawing Sheets

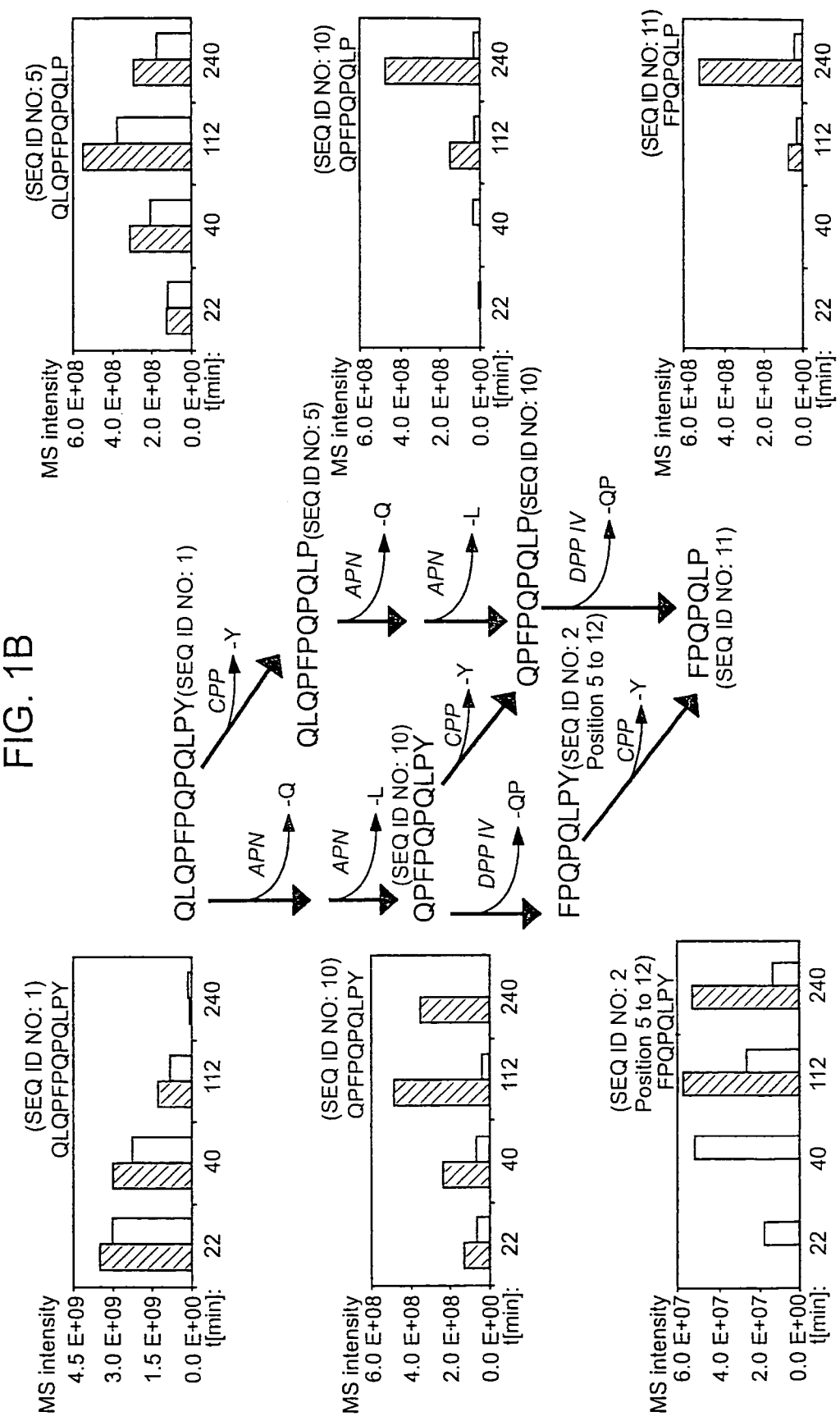

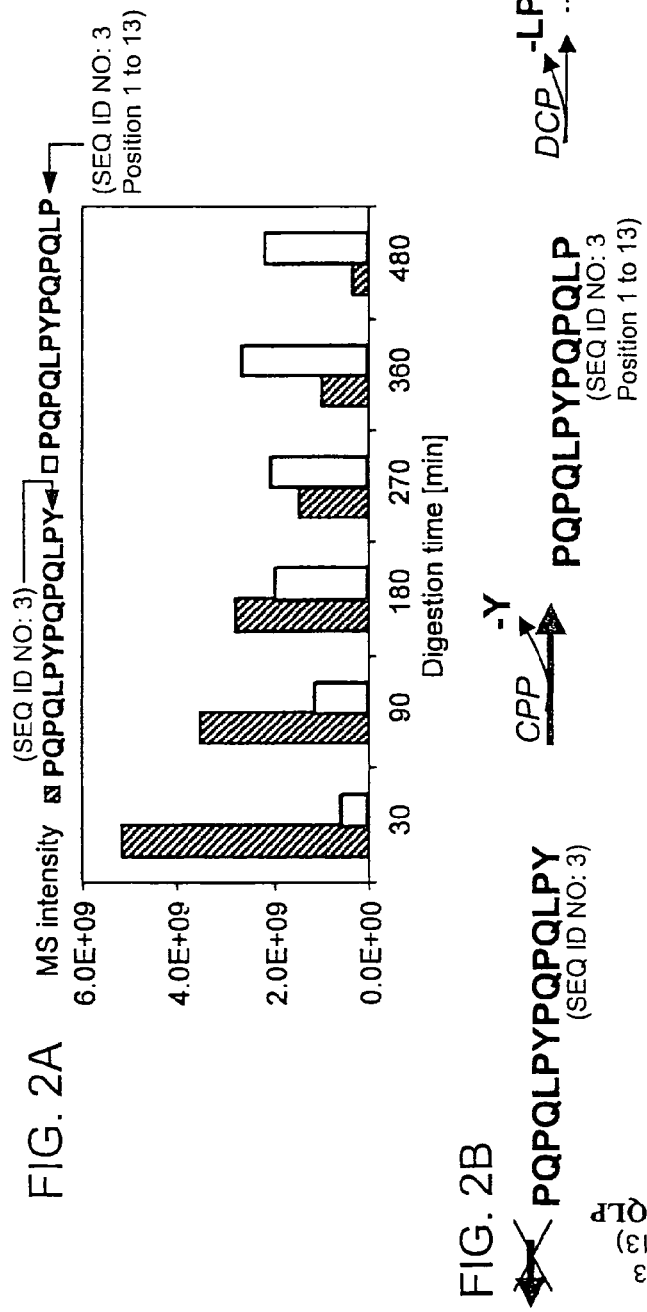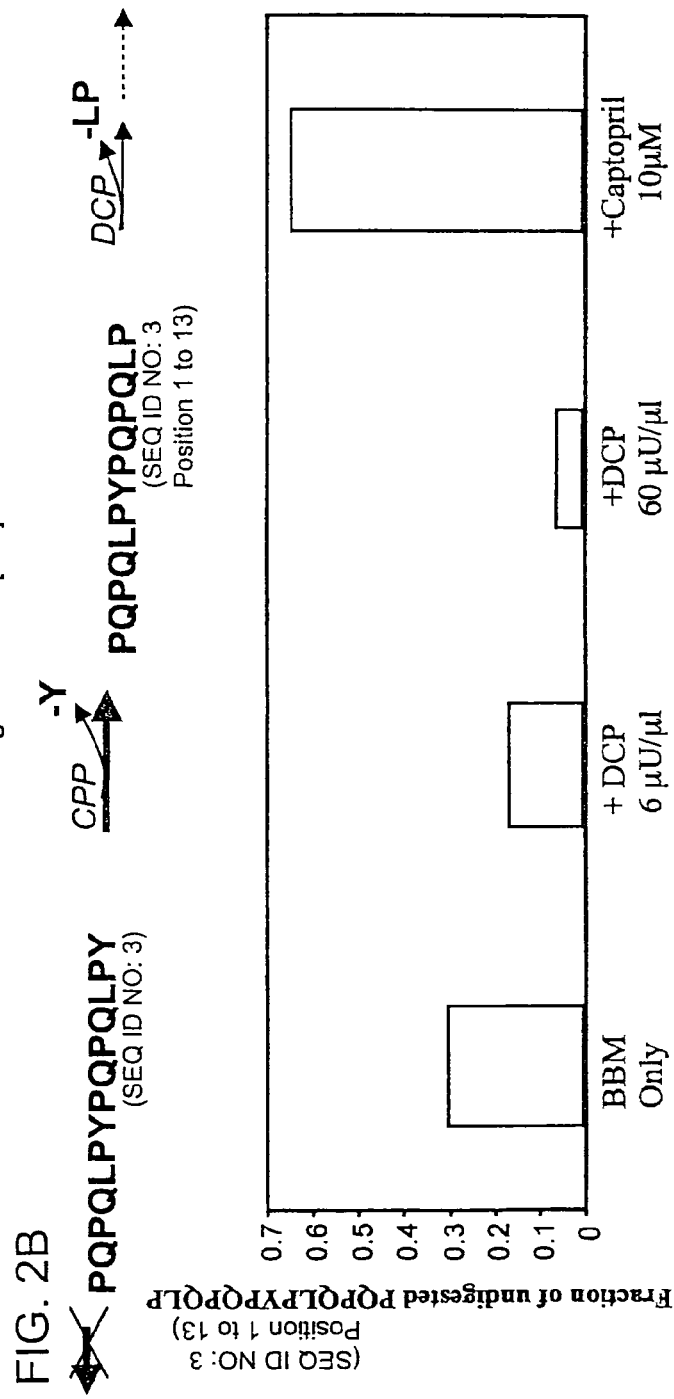
FIG. 2A
FIG. 2B

A

B

PEPTIDES FOR DIAGNOSTIC AND THERAPEUTIC METHODS FOR CELIAC SPRUE

FEDERALLY-SPONSORED RESEARCH OR DEVELOPMENT

This invention was made with Government support under contract 9910949 awarded by the National Science Foundation. The Government has certain rights in this invention.

In 1953, it was first recognized that ingestion of gluten, a common dietary protein present in wheat, barley and rye causes disease in sensitive individuals. Gluten is a complex mixture of glutamine- and proline-rich glutenin and prolamine molecules, which is thought to be responsible for disease induction. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European populations.

A related disease is dermatitis herpetiformis, which is a chronic eruption characterized by clusters of intensely pruritic vesicles, papules, and urticaria-like lesions. IgA deposits occur in almost all normal appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Celiac Sprue is generally considered to be an autoimmune disease and the antibodies found in the serum of the patients support a theory of an immunological nature of the disease. Antibodies to tissue transglutaminase (tTG) and gliadin appear in almost 100% of the patients with active CS, and the presence of such antibodies, particularly of the IgA class, has been used in diagnosis of the disease.

The large majority of patients express the HLA-DQ2 [DQ (a1*0501, b1*02)] and/or DQ8 [DQ(a1*0301, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villous atrophy of the small intestine.

At the present time there is no good therapy for the disease, except to completely avoid all foods containing gluten. Although gluten withdrawal has transformed the prognosis for children and substantially improved it for adults, some people still die of the disease, mainly adults who had severe disease at the outset. An important cause of death is lymphoreticular disease (especially intestinal lymphoma). It is not known whether a gluten-free diet diminishes this risk. Apparent clinical remission is often associated with histologic relapse that is detected only by review biopsies or by increased EMA titers.

Gluten is so widely used, for examples in commercial soups, sauces, ice creams, hot dogs, etc., that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

Current diagnostic methods for Celiac Sprue are expensive and not very accurate. These methods include ELISA-based methods in which either anti-gliadin or anti-tTG antibodies in the patient's serum are detected and in which T cell proliferation upon stimulation with gliadin is observed. Often, however, these methods are not sensitive enough to detect the diagnostic antibodies in the blood or, as is the case for T cell proliferation assays, are deemed to be too expensive for routine use. Typically, even if an individual tests positive in the diagnostic test, the individual must be re-challenged with gliadin (typically after maintaining a gluten-free diet for an extended period of time) and examined by endoscopy, an invasive and often painful procedure.

PCT publication No. WO 01/25793, published 12 Apr. 2001, describes peptides derived from epitope mapping of alpha-gliadin and methods for diagnosing Celiac Sprue using such peptides. Those methods, however, do not appear to be significantly more sensitive than methods currently employed and so do not overcome the limitations of diagnostic methods currently in use.

PCT publication No. WO 02/083722 describes HLA-DQ restricted T cells receptors capable of recognizing prolamine-derived peptides involved in food-related immune enteropathy.

There remains a need for better diagnostic methods for Celiac Sprue, methods that are more sensitive than current methods, that do not require confirmation by endoscopy, and that do not require that an individual be challenged with a gluten-containing diet for accuracy. The present invention addresses this need.

SUMMARY OF THE INVENTION

Methods are provided for diagnosing Celiac Sprue, and/or dermatitis herpetiformis, by detecting multivalent toxic gluten oligopeptides in a patient; antibodies that bind to the toxic gluten oligopeptides; or T cell proliferation elicited by such oligopeptides in a patient. Novel peptides are provided, which interact strongly with gluten reactive T cells and/or HLA molecules. Certain peptides, particularly modified peptides, are shown to bind strongly to the HLA molecule, without activating T cells, thereby blocking reactivity. Such peptides find use in diagnostic and therapeutic methods.

In one aspect, the present invention provides methods for treating Celiac Sprue and/or dermatitis herpetiformis and the symptoms thereof by administration of an HLA-binding peptide inhibitor to the patient. In one embodiment, the HLA-binding peptide inhibitor employed in the method is an analog of an immunogenic gluten peptide, where an immunogenic gluten peptide is altered by the replacement of one or more amino acids, where the replacement may be another naturally occurring amino acid, non-naturally occurring amino acids, modified amino acids, amino acid mimetics, and the like. Analogs of immunogenic gluten peptides that (i) retain the ability to bind tightly to HLA molecules; (ii) retain the proteolytic stability of these peptides; but (iii) are unable to activate disease-specific or other T cells, are useful agents to treat Celiac Sprue.

In another aspect, the present invention provides novel HLA-binding peptide inhibitors and methods for treating Celiac Sprue and/or dermatitis herpetiformis by administering those compounds.

In another aspect, the invention provides pharmaceutical formulations comprising an HLA-binding peptide inhibitor and a pharmaceutically acceptable carrier. In one embodiment, such formulations comprise an enteric coating that allows delivery of the active agent to the intestine, and the agents are stabilized to resist digestion or acid-catalyzed modification in acidic stomach conditions. In another embodiment, the formulation also comprises one or more glutenases, as described in U.S. Provisional Application 60/392,782 filed Jun. 28, 2002; and U.S. Provisional Application 60/428,033, filed Nov. 20, 2002, both of which are incorporated herein by reference. The invention also provides methods for the administration of enteric formulations of one or more HLA-binding peptide inhibitors to treat Celiac Sprue.

These and other aspects and embodiments of the invention and methods for making and using the invention are described in more detail in the description of the drawings and the invention, the examples, the claims, and the drawings that follow.

BRIEF DESCRIPTION OF THE DRAWINGS

FIGS. 1A-1B. Brush border membrane catalyzed digestion of the immunodominant gliadin peptide. FIG. 1A: LC-MS traces of (SEQ ID NO:1) QLQPFPQPQLPY after digestion with 27 ng/µl rat brush border membrane (BBM) protein for the indicated time. Reaction products were separated by reversed phase HPLC and detected by mass spectroscopy (ion counts m/z=300-2000 g/mol). The indicated peptide fragments were confirmed by characteristic tandem MS fragmentation patterns. The SEQ ID NO:2 pyroQLQPFPQPQLPY peak corresponds to an N-terminally pyroglutaminated species, which is generated during HPLC purification of the synthetic starting material. FIG. 1B Abundance of individual digestion products as a function of time. The peptide fragments in FIG. 1A were quantified by integrating the corresponding MS peak area (m/z=300-2000 g/mol). The resulting MS intensities are plotted as a function of digestion time (with BBM only, colored bars). The digestion experiment was repeated in the presence of exogenous DPP IV from *Aspergillus fumigatus* (Chemicon International, CA, 0.28 µU DPP IV/ng BBM protein) and analyzed as above (open bars). The relative abundance of different intermediates could be estimated from the $UV_{280}$ traces and control experiments using authentic standards. The inserted scheme shows an interpretative diagram of the digestion pathways of (SEQ ID NO:1) QLQPFPQPQLPY and its intermediates, the BBM peptidases involved in each step, and the amino acid residues that are released. The color code for labeling the peptides is similar to that used in A. The preferred breakdown pathway is indicated in bold. APN=aminopeptidase N, CPP=carboxypeptidase P, DPP IV=dipeptidyl dipeptidase IV.

FIG. 2A-2B. C-terminal digestion of the immunodominant gliadin peptide by brush border membrane. FIG. 2A: (SEQ ID NO:3) PQPQLPYPQPQLPY was digested by 27 ng/µl brush border membrane (BBM) protein preparations for the indicated time and analyzed as in FIG. 1A. The identity of the starting material and the product (SEQ ID NO:4) PQPQLPYPQPQLP was corroborated by MSMS fragmentation. The intrinsic mass intensities of the two peptides were identical, and the $UV_{280}$ extinction coefficient of (SEQ ID NO:4) PQPQLPYPQPQLP was half of the starting material in accordance with the loss of one tyrosine. All other intermediates were below ≦1%. The scheme below shows the proposed BBM digestion pathway of (SEQ ID NO:3) PQPQLPYPQPQLPY with no observed N-terminal processing (crossed arrow) and the removal of the C-terminal tyrosine by carboxypeptidase P (CPP) in bold. Further C-terminal processing by dipeptidyl carboxypeptidase (DCP) was too slow to permit analysis of the subsequent digestion steps (dotted arrows). FIG. 2B: Influence of dipeptidyl carboxypeptidase on C-terminal digestion. (SEQ ID NO:3) PQPQLPYPQPQLPY in phosphate buffered saline:Tris buffered saline=9:1 was digested by BBM alone or with addition of exogenous rabbit lung DCP (Cortex Biochemicals, CA) or captopril. After overnight incubation, the fraction of accumulated SEQ ID NO:4) PQPQLPYPQPQLP (compared to initial amounts of (SEQ ID NO:3) PQPQLPYPQPQLPY at t=min) was analyzed as in FIG. 2A, but with an acetonitrile gradient of 20-65% in 6-35 minutes.

DETAILED DESCRIPTION OF THE EMBODIMENTS

Figure 1A:
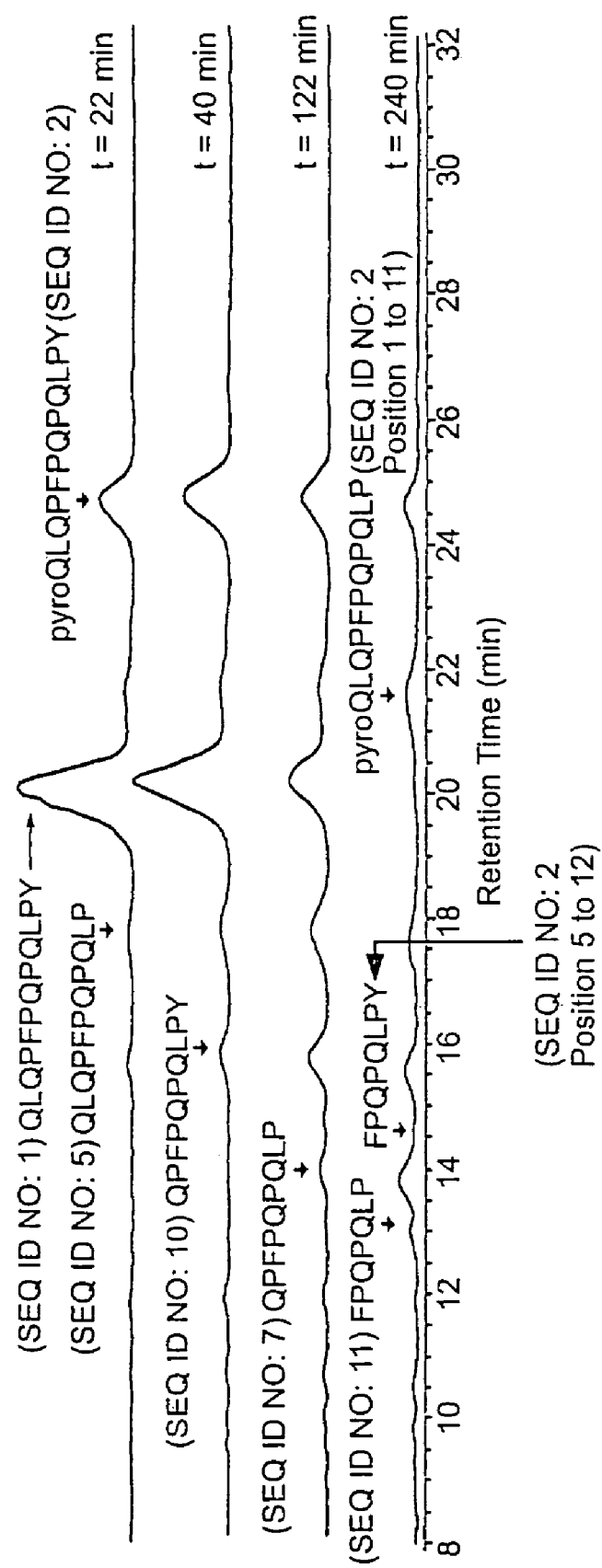
Figure 3:
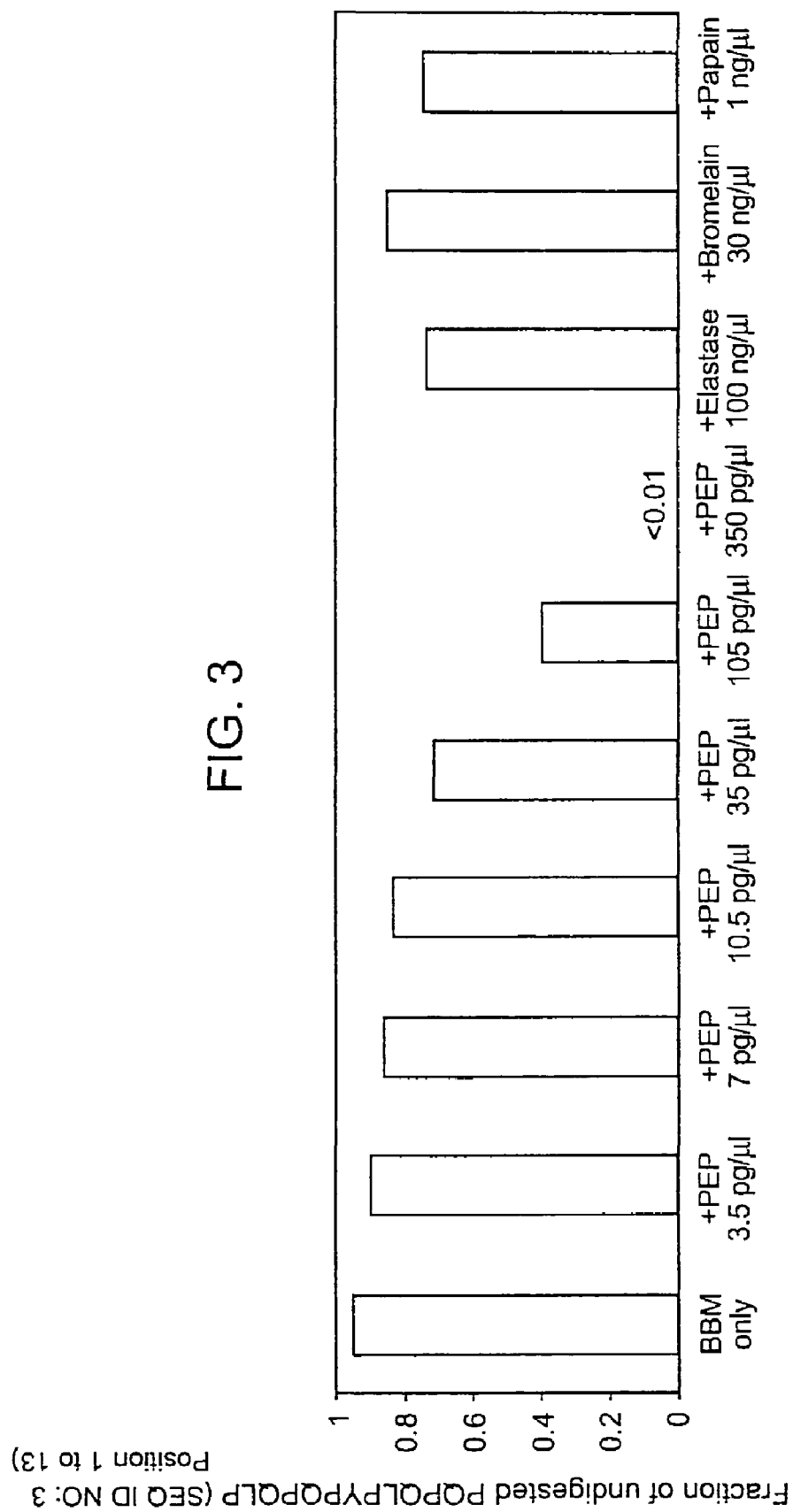
FIG. 3. Dose dependent acceleration of brush border mediated digestion by exogenous endoproteases. As seen from FIG. 2A-2B, the peptide (SEQ ID NO:4) PQPQLPYPQPQLP is stable toward further digestion. This peptide was digested with 27 ng/µl brush border membranes, either alone, with increasing amounts of exogenous prolyl endopeptidase (PEP, specific activity 28 µU/pg) from *Flavobacterium meningosepticum* (US Biological, MA), or with additional elastase (E-1250, Sigma, MO), bromelain (B-5144, Sigma, MO) or papain (P-5306, Sigma, MO). After one hour, the fraction of remaining (SEQ ID NO:4) PQPQLPYPQPQLP (compared to the initial amount at t=0 min) was analyzed and quantified as in FIG. 1.

Celiac Sprue and/or dermatitis herpetiformis are diagnosed by detecting antibodies that bind to digestion refractory gluten oligopeptides and/or T-cell proliferation produced by such oligopeptides in Celiac Sprue individuals. Gluten oligopeptides are highly resistant to cleavage by gastric and pancreatic peptidases such as pepsin, trypsin, chymotrypsin, and the like. —By providing for detection of such gluten oligopeptides; of antibodies specifically reactive thereto; and/or of T-cell proliferation produced by such oligopeptides in individuals, improved methods of diagnosing Celiac Sprue and/or dermatitis herpetiformis are provided.

Celiac Sprue and/or dermatitis herpetiformis may also be treated by interfering with HLA binding of immunogenic gluten peptides. Therapeutic benefit can also be enhanced in some individuals by increasing the digestion of gluten oligopeptides, whether by pretreatment of foodstuffs to be ingested or by administration of an enzyme capable of digesting the gluten oligopeptides, together with administration of an HLA-binding peptide inhibitor. Gluten oligopeptides are highly resistant to cleavage by gastric and pancreatic peptidases such as pepsin, trypsin, chymotrypsin, and the like, and their prolonged-presence in the digestive tract can induce an autoimmune response. The antigenicity of gluten oligopeptides and the ill effects caused by an immune response thereto can be decreased by administration of an HLA-binding peptide inhibitor. Such inhibitors are analogs of immunogenic gluten peptides and (i) retain the ability to bind tightly to HLA molecules; (ii) retain the proteolytic stability of these peptides; but (iii) are unable to activate disease-specific or other T cells.

In some embodiments and for some individuals, the methods of the invention remove the requirement that abstention from ingestion of glutens be maintained to keep the disease in remission. The compositions of the invention include formulations of tTGase inhibitors that comprise an enteric coating that allows delivery of the agents to the intestine in an active form; the agents are stabilized to resist digestion or alternative chemical transformations in acidic stomach conditions. In another embodiment, food is pretreated or combined with glutenase, or a glutenase is co-administered (whether in time or in a formulation of the invention) with an HLA-binding peptide inhibitor of the invention.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease, particularly diminution of the severity of such symptoms as fatigue, chronic diarrhea, malabsorption of nutrients, weight loss, abdominal distension, and anemia. Other disease indicia include the presence of antibodies specific for glutens, antibodies specific for tissue transglutaminase, the presence of pro-inflammatory T cells and cytokines, and degradation of the villus structure of the small intestine. Application of the methods and compositions of the invention can result in the improvement of any and all of these disease indicia of Celiac Sprue.

Patients that can benefit from the present invention include both adults and children. Children in particular benefit from prophylactic treatment, as prevention of early exposure to toxic gluten peptides can prevent development of the disease into its more severe forms. Children suitable for prophylaxis in accordance with the methods of the invention can be identified by genetic testing for predisposition, e.g. by HLA typing; by family history, and by other methods known in the art. As is known in the art for other medications, and in accordance with the teachings herein, dosages of the HLA-binding peptide inhibitors of the invention can be adjusted for pediatric use.

Because most proteases and peptidases are unable to hydrolyze the amide bonds of proline residues, the abundance of proline residues in gliadins and related proteins from wheat, rye and barley can constitute a major digestive obstacle for the enzymes involved. This leads to an increased concentration of relatively stable gluten derived oligopeptides in the gut. These stable gluten derived oligopeptides, called "immunogenic oligopeptides" herein, bind to MHC molecules, including HLA HLA-DQ2 or DQ8 molecules, to stimulate an immune response that results in the autoimmune disease aspects of Celiac Sprue. In some cases the enzyme tissue transglutaminase selectively deamidates certain glutamine residues in these peptides, thereby enhancing their potency for the DQ2 ligand binding pocket.

Peptides of particular interest for these purposes are analogs of SEQ ID NO:12 LQLQPF-PQPQLPYPQPQLPYPQPQLPYPQPQPF. Such analogs may comprise one or more of the modifications set forth herein. Analogs may be truncated of 5, 10, 12, 13 or more amino acids, which truncation may be from the amino or the carboxy terminus. Analogs may be deamidated at one, two, three or more glutamine residues, by substitution with glutamic acid at these positions, where deamidation of residues 10, 17 and 24 are of particular interest. Analogs may be substituted at one, two three or more leucine residues for lysine, where substitution of positions 11, and 18 are of particular interest; and/or modification of the substituted lysine residues with a sterically hindered conjugate to the ε-amine group.

Deamidated, and in some instances truncated, analogs of SEQ ID NO:12 include:

| ID Number | | |
|---|---|---|
| SEQ ID NO: 12 | 1 | LQLQPFPQPELPYPQPELPYPQPELPYPQPQPF |
| SEQ ID NO: 17 | 2 | PFPQPELPY |
| SEQ ID NO: 18 | 3 | PQPELPYPQ |
| SEQ ID NO: 19 | 4 | LQLQPFPQPELPYPQ |
| SEQ ID NO: 20 | 5 | LQLQPFPQPELPYPQPELPY |
| SEQ ID NO: 21 | 6 | PQPELPYPQPELPY |
| SEQ ID NO: 22 | 7 | PQPELPYPQPELPYPQPELPY |
| SEQ ID NO: 23 | 8 | PFPQPELPYPQPELPYPQPELPYPQPQP |
| SEQ ID NO: 24 | 9 | LQPFPQPELPYPQPELPYPQPELPYPQPQP |
| SEQ ID NO: 25 | 10 | QLQPFPQPELPYPQPELPYPQPELPYPQPQP |
| SEQ ID NO: 26 | 11 | LQLQPFPQPELPYPQPQLPYPQPQLPYPQPQPF |
| SEQ ID NO: 27 | 12 | LQLQPFPQPELPYPQPELPYPQPQLPYPQPQPF |
| SEQ ID NO: 28 | 13 | LQLQPFPQPQLPYPQPQLPYPQPELPYPQPQPF |
| SEQ ID NO: 29 | 14 | LQLQPFPQPELPYPQPELPYPQPQLPYPQPQPF |
| SEQ ID NO: 30 | 15 | LQLQPFPQPELPYPQPQLPYPQPELPYPQPQPF |
| SEQ ID NO: 31 | 16 | LQLQPFPQPQLPYPQPELPYPQPELPYPQPQPF |

It can be seen from these sequences that analogs comprising various combinations of deamidated residues can be produced (SEQ ID NO:17-23), and will bind to the HLA molecule DQ2. Additional modifications include deletion of terminal residues, for example SEQ ID NO:24-SEQ ID NO:30. The antigenic response of the 33 mer is principally centered around the (SEQ ID NO:31) (SEQ ID NO: 18) PQPELPYPQ epitope (residues 7-15), but that the N-terminal sequence (SEQ ID NO:32) LQLQPF as well as a C-terminally located secondary Glu (e.g. E17 or E24) residue further enhance DQ2 affinity of the 33 mer.

In one embodiment of the invention, a peptide of at least about 14 amino acids, at least 18 amino acids, at least 20 amino acids, at least 22 amino acids, and not more than about 33 amino acids, not more than about 28, not more than about 26, or not more than about 24 amino acids is provided, wherein said peptide comprises the epitope sequence (SEQ ID NO: 18) PQPELPYPQ. The peptide may optionally comprise as the amino terminal sequence, (SEQ ID NO:32), LQLQPF. For example, such a peptide may comprise the sequence of SEQ ID NO:27, and may further comprise a C-terminally located secondary glu residue. In some embodiments, the carboxy terminal sequence is SEQ ID NO:44 PELPY, or SEQ ID NO:45 PEKPY, e.g. (SEQ ID NO:34), LQLQPFPQPELPYPQPEKPY In another embodiment, the peptide of interest described above comprises the epitope sequence (SEQ ID NO:43) PQPEKPYPQ, wherein the leucine has been replaced with a lysine residue. Such peptides may optionally comprise as the amino terminal sequence, SEQ ID NO:32, LQLQPF, for example SEQ ID NO:33 LQLQPFPQPEKPYPQPELPY. Such peptide may optionally comprise a C-terminally located secondary glu residue. In some embodiments, the carboxy terminal sequence is SEQ ID NO:44 PELPY, or SEQ ID NO:45 PEKPY, for example SEQ ID NO:35 LQLQPFPQPE-KPYPQPEKPY.

The ε-amine of the lysine is generally reactive to electrophiles, and can readily by modified. The lysine residues in the peptides described above may be conjugated to a group that provides for steric hindrance of interactions between the peptide and a cognate receptor. Such conjugates may include, without limitation, succinic acid; glutaric acid; γ-aminobutyric acid; benzyloxycarbonyl group; t-Butoxycarbonyl group; 9-fluorenylmethoxycarbonyl group; phthalimides; polyethylene glycol; secondary and tertiary amines. Peptides thus modified have been found to bind very well to HLA antigens, but do not activate T cells that proliferate in response to SEQ ID NO:12. Such peptides therefore find use as inhibitors of immune responses involved in Celiac Sprue and/or dermatitis herpetiformis.

Peptides as described above, including, without limitation, those comprising or consisting of SEQ ID NO:43, SEQ ID NO:33, SEQ ID NO:35, may additionally be substituted with cysteine. Sites for cysteine substitution include the sites of lysine substitution (residue 11 and 18 with respect to SEQ ID NOL35). Such analogs are transformed into DQ2 blockers through intramolecular cyclization via disulfide bond formation. Cyclic DQ2 binding molecules may further be modified by altering the bridge lengths, e.g. replacing cysteine with analogues such as homocysteine. More stable analogues are prepared by replacing disulfide bonds with other flexible cyclization tethers. Two strategies of interest are replacement of disulfide bridges with thioether linkages [Robey, F. A. (2000) Selective and Facile Cyclization of Nchloroacetylated Peptides from the C4 Domain of HIV Gp120 in LiCl/DMF Solvent Systems. *J. Peptide Res.* 56, 115-120; Oligino, L.; Lung, F.-D. T.; Sastry, L.; Bigelow, J.; Cao, T.; Curran, M.; Burke, T. R., Jr.; Wang, S.; Krag, D.; Roller, P. P.; King, C. R. (1997) Nonphosphorylated Peptide Ligands for the Grb2 Src Homology 2 Domain. *J. Biol. Chem.* 272, 29046-29052] and olefin metathesis [Blackwell, H. E.; Grubbs, R. H. (1998) Highly Efficient Synthesis of Covalently Cross-linked Peptide Helices by Ring-Closing Metathesis. *Angew. Chem. Int. Ed.* 37, 3281-3284; Schafmeister C. E.; Po, J.; Verdine, G. L. (2000) An All-Hydrocarbon Cross-Linking System for Enhancing the Helicity and Metabolic Stability of Peptides. *J. Am. Chem. Soc.* 122, 5891-5892]. Alternatively, a wide range of bis-alkylating agents such as dibromoketones are used, since the resulting macrocyclic products, if active, will contain an orthogonal ketone functional group for further modification In another embodiment, an immunogenic gluten oligopeptide analog is an analog of a peptide that comprises at least about 8 residues, and may comprise at least about 10 residues; at least about 11 residues, at least about 12 residues, at least about 13 residues, at least about 14 residues, or more, where the term "residue" refers to naturally occurring amino acids, non-naturally occurring amino acids, and amino acid mimetics or derivatives; and where the gluten peptide is altered by the replacement of one or more amino acids. The replacement may be another naturally occurring amino acid, non-naturally occurring amino acids, modified amino acids, amino acid mimetics, and the like; and may further be derivitized to further reduce the affinity of these ligands for disease-specific T cell receptors. The sequence of immunogenic gluten oligopeptides can be determined by one of skill in the art. Immunogenic gliadin oligopeptides are peptides derived during normal human digestion of gliadins and related storage proteins as described above, from dietary cereals, e.g. wheat, rye, barley, and the like. Such oligopeptides act as antigens for T cells in Celiac Sprue. For binding to Class II MHC proteins, immunogenic peptides are usually from about 8 to 20 amino acids in length, more usually from about 10 to 18 amino acids. Such peptides may include PXP motifs, such as the motif (SEQ ID NO: 8) PQPQLP. Determination of whether an oligopeptide is immunogenic for a particular patient is readily determined by standard T cell activation and other assays known to those of skill in the art.

Among gluten proteins with potential harmful effect to Celiac Sprue patients are included the storage proteins of wheat, species of which include *Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi*; etc. A review of the genes encoding wheat storage proteins may be found in Colot (1990) *Genet Eng* (N Y) 12:225-41. Gliadin is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be identified using routine methods of molecular biology. Examples of gliadin sequences include but are not limited to wheat alpha gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

Among the immunogenic gluten oligopeptides that may be modified to generate an HLA-binding peptide inhibitor are included the peptide sequence (SEQ ID NO:44) QLQPF-PQPELPYP; the sequence (SEQ ID NO:36) PQPELPY; the sequence (SEQ ID NO:46) PFPQPELPYP, (SEQ ID NO:47) PQPELPYPQPQLP, (SEQ ID NO:48) PQQSFPEQQPP, (SEQ ID NO:49) VQGQGIIQPEQPAQ, (SEQ ID NO:50) FPEQPQQPYPQQP, (SEQ ID NO:51) FPQQPEQPYPQQP, (SEQ ID NO:52) FSQPEQEFPQPQ and longer peptides containing such sequences or multiple copies of such sequences. Gliadins, secalins and hordeins contain several (SEQ ID NO:53) PQPQLPY sequences or sequences similar thereto rich in Pro-Gln residues that are high-affinity substrates for tTGase. The tTGase catalyzed deamidation of such sequences increases their affinity for HLA-DQ2, the class II MHC allele present in >90% Celiac Sprue patients. Presentation of these deamidated sequences by DQ2 positive antigen presenting cells effectively stimulates proliferation of gliadin-specific T cells from intestinal biopsies of most Celiac Sprue patients, providing evidence for the proposed mechanism of disease progression in Celiac Sprue.

Analog oligopeptides of the invention comprise at least one difference in amino acid sequence from a native gluten peptide, by the replacement of an amino acid with a different amino acid; a non-naturally occurring amino acid, a peptidomimetics, substituted amino acid, and the like. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine, ornithine and homoserine. Also included with the scope of the present invention are amino acids that have been altered by chemical means such as methylation (e.g., α-methylvaline), deamidation, amidation of the C-terminal amino acid by an alkylamine such as ethylamine, ethanolamine, and ethylene diamine, and acylation or methylation of an amino acid side chain function (e.g., acylation of the epsilon amino group of lysine), deimination of arginine to citrulline, isoaspartylation, or phosphorylation on serine, threonine, tyrosine or histidine residues. Importantly, each of these altered amino acids provide a functional handle, e.g. amine, alcohol, aryl halide, and the like, which can be regioselectively derivatized to further reduce the affinity of these ligands for disease-specific T cell receptors. Peptide analogs may be further derivatized with substitutions, including, without limitation, ethers, amines, esters, amides, carbonates, carbamates, carbazates, ureas and C-C coupled derivatives. Other examples include oxidation of alcohols to ketones, followed by further modifications of the resulting carbonyl group, e.g. via preparation of oximes) or the carbon atom adjacent to the ketone. Such derivatives are encompassed by the term "analog".

The proteolytic stability of gluten oligopeptides can be attributed, at least in part, to the presence of PXP motifs, which are resistant to enzymatic degradation. Preferred analogs of immunogenic gluten oligopeptides will comprise one or more proline residues, and may comprise one or more PXP motifs.

One inhibitor of interest is an oligopeptide or peptidomimetic that comprises the sequence PXPQPELPY, where X is Gly, Ala, Tyr, Trp, Arg, Lys, p-iodo-Phe, 3-iodo-Tyr, p-amino-Phe, 3-amino-Tyr, hydroxylysine, ornithine, Asp, Glu, or any residue that is substantially bulkier or hydrophilic than Phe. Examples of suitable modifications include ethers, amines, esters, amides, carbonates, carbamates, carbazates, ureas and C-C coupled derivatives. Other examples include oxidation of alcohols to ketones, followed by further modifications of the resulting carbonyl group (e.g. via preparation of oximes) or the carbon atom adjacent to the ketone. The peptide may comprise modifications that increase binding potency to an MHC molecule, by varying residues that facilitate peptide docking into the binding cleft. Examples of such residues include Gln-4, Glu-6, Leu-7, and Tyr-9 (numbering based on the epitope (SEQ ID NO: 17) PFPQPELPY). Each of these residues interacts closely with several residues in the DQ2 binding pocket. By using structure-based molecular design methods, these interactions can be optimized.

Another inhibitor of interest is a oligopeptide or peptidomimetic that comprises the sequence PFPQX$_1$ELX$_2$Y, where X$_1$ and X$_2$ are independently selected from 4-hydroxy-Pro (either isomer at C-4), 4-amino-Pro (either isomer at C-4), or 3-hydroxy-Pro (either isomer at C-3), and proline, with the proviso that at least one of X$_1$ and X$_2$ is a residue other than proline.

As described above, the sequence of gluten peptides may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated, where the polyethyleneoxy group provides for enhanced lifetime in the blood stream. The peptides may also be combined with other proteins, such as the Fc of an IgG isotype, which may be complement binding, with a toxin, such as ricin, abrin, diphtheria toxin, or the like, or with specific binding agents that allow targeting to specific moieties on a target cell.

Modifications of interest that do not alter primary sequence include chemical derivatization of polypeptides, e.g., acetylation, acylation, carboxylation, etc. Also embraced are sequences that have phosphorylated amino acid residues, e.g. phosphotyrosine, phosphoserine, or phosphothreonine.

Also included in the subject invention are peptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

Peptides and peptide analogs may be synthesized by standard chemistry techniques, including synthesis by automated procedure. In general, peptide analogs are prepared by solid-phase peptide synthesis methodology which involves coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminus. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the peptide consists essentially of a polypeptide sequence as set forth in any one of the SEQ ID NOs provided herein. By "consisting essentially of" in the context of a polypeptide described herein, it is meant that the polypeptide is composed of the gluten sequence, which sequence may be flanked by one or more amino acid or other residues that do not materially affect the basic characteristic(s) of the polypeptide.

Interactions with Immune System Receptors

Preferably, antigenic oligopeptides of interest for use in the methods of the invention are as described above, and comprise at least one epitope. As used herein, the term "epitope" refers to the portion of an antigen bound by an antibody or T cell receptor, which portion is sufficient for high affinity binding. In polypeptide antigens, generally a linear epitope for recognition will be at least about 7 amino acids in length, and may be 8 amino acids, 9 amino acids, 10 amino acids, or more.

Antibodies may recognize linear determinants or conformational determinants formed by non-contiguous residues on an antigen, and an epitope can therefore require a larger fragment of the antigen to be present for binding, e.g. a protein domain, or substantially all of a protein sequence. The binding site of antibodies typically utilizes multiple non-covalent interactions to achieve high affinity binding. While a few contact residues of the antigen may be brought into close proximity to the binding pocket, other parts of the antigen molecule can also be required for maintaining a conformation that permits binding. In order to consider an antibody interaction to be "specific", the affinity will be at least about $10^{-7}$ M, usually about $10^{-8}$ M to $10^{-9}$ M, and may be up to $10^{-11}$ M or higher for the epitope of interest. It will be understood by those of skill in the art that the term "specificity" refers to such a high affinity binding, and is not intended to mean that the antibody cannot bind to other molecules as well. One may find cross-reactivity with different epitopes, due, e.g. to a relatedness of antigen sequence or structure, or to the structure of the antibody binding pocket itself.

The T cell receptor recognizes a more complex structure than antibodies, and requires both a major histocompatibility antigen binding pocket and an antigenic peptide to be present. The binding affinity of T cell receptors is lower than that of antibodies, and will usually be at least about $10^{-4}$ M, more usually at least about $10^{-5}$ M.

Affinity and stability are different measures of binding interaction. The definition of affinity is a thermodynamic expression of the strength of interaction between a single antigen binding site and a single antigenic determinant (and thus of the stereochemical compatibility between them). Affinity does not change with valency, because it is the measure of interaction between a single binding site and a single antigenic determinant. In contrast to affinity, avidity (which relates to the $t_{1/2}$ of an interaction) is defined as the strength of binding, usually of a small molecule with multiple binding sites by a larger molecule, and in particular, the binding of a complex antigen by an antibody. Therefore, it is avidity that takes into account the effect of multiple interactions, and it is the change in avidity that may provides the hyperantigenicity observed with the oligopeptide of SEQ ID NO:12.

Certain of the gluten oligopeptides analogs described herein are useful in stimulating T cells from Celiac Sprue patients for diagnostic purposes, while others are shown to inhibit T cell stimulation. Such peptides are provided by the present invention in isolated and highly purified forms. Further, the gluten oligopeptides analogs described herein are useful in diagnostic assays for detecting antibodies against such oligopeptides or for producing antibodies that bind specifically to such oligopeptides for their detection.

Diagnostic Methods

The present invention provides a variety of methods for diagnosing Celiac Sprue. In one embodiment, the diagnosis involves detecting the presence of a gluten oligopeptides digestion product, e.g. SEQ ID NO:12; deamidated counterparts there; a tTGase-linked counterpart thereof; etc., in a tissue, bodily fluid, or stool of an individual. The detecting step can be accomplished by use of a reagent, e.g. an antibody, that recognizes the indicated antigen, or by a cell that proliferates in the presence of the indicated antigen and suitable antigen presenting cells, wherein said antigen presenting cells are compatible with the MHC type of the proliferating cell, e.g. allogeneic cells, autologous cells, etc.

In another embodiment, the diagnosis involves detecting the presence of an antibody, one or more T cells reactive with the 33-mer or a deamidated counterpart thereof, or a tTGase-linked counterpart thereof in a tissue, bodily fluid, or stool of an individual. In one embodiment, an antibody is detected by, for example, an agglutination assay using an antigen provided by the present invention. In another embodiment, a T cell is detected by its proliferation in response to exposure to a multivalent gluten oligopeptide provided by the present invention and presented by autologous or suitable allogeneic antigen presenting cells.

In one aspect, the methods and reagents of the present invention are capable of detecting the toxic oligopeptides of gluten proteins of wheat, barley, oats and rye remaining after digestion or partial digestion of the same by a Celiac Sprue individual. Gluten is the protein fraction in cereal dough, which can be subdivided into glutenins and prolamines, which can be further subclassified as gliadins, secalins, hordeins, avenins from wheat, rye, barley and oat, respectively. For further discussion of gluten proteins, see the review by Wieser (1996) Acta Paediatr Suppl. 412:3-9; herein incorporated by reference. Among gluten proteins of interest are included the storage proteins of wheat, species of which include *Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi*; and the like. A review of the genes encoding wheat storage proteins may be found in Colot (1990) *Genet Eng* (NY) 12:225-41.

Of particular interest is gliadin, which is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be obtained using routine methods of molecular biology. Examples of sequenced gliadins include wheat alpha gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

For the purposes of the present invention, toxic gliadin oligopeptides are peptides derived during normal digestion of gliadins and related storage proteins as described above, from dietary cereals, e.g. wheat, rye, barley, and the like, by a Celiac Sprue individual. Such oligopeptides are believed to act as antigens for T cells in Celiac Sprue individuals. For binding to Class II MHC proteins, immunogenic peptides are usually from about 6 to 20 amino acids in length, more usually from about 10 to 18 amino acids, and as demonstrated herein, a particularly stimulatory toxic gliadin oligopeptide is the multivalent 33-mer described above. Such peptides include PXP motifs, for example the motif PQPQLP (SEQ ID NO:8). Determination of whether an oligopeptide is immunogenic for a particular patient is readily determined by standard T cell activation assays known to those of skill in the art. Illustrative toxic gliadin oligopeptides of the invention are described in Examples 1 and 2 below. The 33-mer gliadin oligopeptide of Example 2 and its deamidated counterpart formed by tTGase are preferred toxic gliadin oligopeptides of the invention.

Samples may be obtained from patient tissue, which may be a mucosal tissue, including but not limited to oral, nasal, lung, and intestinal mucosal tissue, a bodily fluid, e.g. blood, sputum, urine, phlegm, lymph, and tears. One advantage of the present invention is that the antigens provided are such potent antigens, both for antibody-binding and T-cell stimulation, that the diagnostic methods of the invention can be employed with samples (tissue, bodily fluid, or stool) in which a Celiac Sprue diagnostic antibody, peptide, or T cell is present in very low abundance. This allows the methods of the invention to be practiced in ways that are much less invasive, much less expensive, and much less harmful to the Celiac Sprue individual.

Patients may be monitored for the presence of reactive T cells, using one or more multivalent oligopeptides as described above. The presence of such reactive T cells indicates the presence of an on-going immune response. The antigen used in the assays is a gluten oligopeptide analog as described above; including, without limitation, SEQ ID NO:12; deamidated counterparts; tTGase fusions thereof; and derivatives. Cocktails comprising multiple oligopeptides; panels of peptides; etc. may be also used. Overlapping peptides may be generated, where each peptide is frame-shifted from 1 to 5 amino acids, thereby generating a set of epitopes.

The diagnosis may determine the level of reactivity, e.g. based on the number of reactive T cells found in a sample, as compared to a negative control from a naive host, or standardized to a data curve obtained from one or more positive controls. In addition to detecting the qualitative and quantitative presence of antigen reactive T cells, the T cells may be typed as to the expression of cytokines known to increase or suppress inflammatory responses. While not necessary for diagnostic purposes, it may also be desirable to type the epitopic specificity of the reactive T cells, particularly for use in therapeutic administration of peptides.

T cells may be isolated from patient peripheral blood, lymph nodes, including peyer's patches and other gut-related lymph nodes, or from tissue samples as described above. Reactivity assays may be performed on primary T cells, or the cells may be fused to generate hybridomas. Such reactive T cells may also be used for further analysis of disease progression, by monitoring their in situ location, T cell receptor utilization, MHC cross-reactivity, etc. Assays for monitoring T cell responsiveness are known in the art, and include proliferation assays and cytokine release assays. Also of interest is an ELISA spot assay.

Proliferation assays measure the level of T cell proliferation in response to a specific antigen, and are widely used in the art. In one such assay, recipient lymph node, blood or spleen cells are obtained at one or more time points after transplantation. A suspension of from about $10^4$ to $10^7$ cells, usually from about $10^5$ to $10^6$ cells is prepared and washed, then cultured in the presence of a control antigen, and test antigens, as described above. The cells are usually cultured for several days. Antigen-induced proliferation is assessed by the monitoring the synthesis of DNA by the cultures, e.g. incorporation of $^3$H-thymidine during the last 18 H of culture.

T cell cytotoxic assays measure the numbers of cytotoxic T cells having specificity for the test antigen. Lymphocytes are obtained at different time points after transplantation. Alloreactive cytotoxic T cells are tested for their ability to kill target cells bearing recipient MHC class I molecules associated with peptides derived from a test antigen. In an exemplary assay, target cells presenting peptides from the test antigen, or a control antigen, are labeled with Na$^{51}$CrO$_4$. The target cells are then added to a suspension of candidate reactive lymphocytes. The cytotoxicity is measured by quantitating the release of Na$^{51}$CrO$_4$ from lysed cells. Controls for spontaneous and total release are typically included in the assay. Percent specific $^{51}$Cr release may be calculated as follows: 100× (release by CTL−spontaneous release)/(total release−spontaneous release).

Enzyme linked immunosorbent assay (ELISA) and ELISA spot assays are used to determine the cytokine profile of reactive T cells, and may be used to monitor for the expression of such cytokines as IL-2, IL-4, IL-5, γIFN, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

In one embodiment of the invention, the presence of reactive T cells is determined by injecting a dose of the 33-mer peptide, or a derivative or fragment thereof as described above, subcutaneously or sub-mucosally into a patient, for example into the oral mucosa (see Lahteenoja et al. (2000) Am. J. Gastroenterology 95:2880, herein incorporated by reference). A control comprising medium alone, or an unrelated protein is usually injected nearby at the same time. The site of injection is examined after a period of time, by biopsy or for the presence of a wheal.

A wheal at the site of injection is compared to that at the site of the control injection, usually by measuring the size of the wheal. The skin test readings may be assessed by a variety of objective grading systems. A positive result for the presence of an immune response will show an increased diameter at the site of polypeptide injection as compared to the control.

Where a biopsy is performed, the specimen is examined for the presence of increased numbers of immunologically active cells, e.g. T cells, B cells, mast cells, and the like. For example, methods of histochemistry and/or immunohistochemistry may be used, as is known in the art. The densities of cells, including antigen specific T cells, mast cells, B cells, etc. may be examined. It has been reported that increased numbers of intraepithelial CD8$^+$ T cells may correlate with gliadin reactivity.

An alternative method relies on the detection of circulating antibodies in a patient. Methods of detecting specific antibodies are well-known in the art. Antibodies specific for multivalent gluten oligopeptides as described above may be used in screening immunoassays. A sample is taken from the patient. Samples, as used herein, include biological fluids such as blood, tears, saliva, lymph, dialysis fluid and the like; organ or tissue culture derived fluids; and fluids extracted from physiological tissues. Also included in the term are derivatives and fractions of such fluids. Blood samples and derivatives thereof are of particular interest.

Measuring the concentration of specific antibodies in a sample or fraction thereof may be accomplished by a variety of specific assays. In general, the assay will measure the reactivity between a patient sample, usually blood derived, generally in the form of plasma or serum. The patient sample may be used directly, or diluted as appropriate, usually about 1:10 and usually not more than about 1:10,000. Immunoassays may be performed in any physiological buffer, e.g. PBS, normal saline, HBSS, dPBS, etc.

In one embodiment, a conventional sandwich type assay is used. A sandwich assay is performed by first attaching the peptide to an insoluble surface or support. The peptide may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently.

The insoluble supports may be any composition to which peptides can be bound, which is readily separated from soluble material, and which is otherwise compatible with the overall method of measuring antibodies. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support i.e. those not occupied by antigen, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Samples, fractions or aliquots thereof are then added to separately assayable supports (for example, separate wells of a microtiter plate) containing support-bound antigenic peptide. Preferably, a series of standards, containing known concentrations of antibodies is assayed in parallel with the samples or aliquots thereof to serve as controls.

Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for antibodies molecules to bind the insoluble antigenic peptide. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing a second receptor specific for the patient antibodies is applied. The receptor may be any compound that binds patient antibodies with sufficient specificity such that it can be distinguished from other components present. In a preferred embodiment, second receptors are antibodies specific for patient antibodies, either monoclonal or polyclonal sera, e.g. mouse anti-human antibodies, mouse anti-dog antibodies, rabbit anti-cat antibodies, etc. Such second stage antibodies may be labeled to facilitate direct, or indirect quantification of binding.

Examples of labels which permit direct measurement of second receptor binding include radiolabels, such as $^3$H or $^{125}$I, fluorescers, dyes, beads, chemilumninescers, colloidal particles, and the like. Examples of labels that permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Alternatively, the second stage may be unlabeled, and a labeled third stage is used. Examples of second receptor/second receptor-specific molecule pairs include antibody/anti-antibody and avidin (or streptavidin)/biotin. Since the resultant signal is thus amplified, this technique may be advantageous where only a small amount of antibodies is present.

After the second stage has bound, the insoluble support is generally again washed free of non-specifically bound molecules, and the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine, which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

Generally the amount of bound antibodies detected will be compared to control samples from normal patients. The presence of increased levels of the antigen specific antibodies is indicative of disease, usually at least about a 5 fold, 10 fold, or 100 fold increase will be taken as a positive reaction.

In some cases, a competitive assay will be used. In addition to the patient sample, a competitor to the antibodies is added to the reaction mix. The competitor and the antibodies compete for binding to the antigenic peptide. Usually, the competitor molecule will be labeled and detected as previously described, where the amount of competitor binding will be proportional to the amount of antibodies present. The concentration of competitor molecule will be from about 10 times the maximum anticipated antibodies concentration to about equal concentration in order to make the most sensitive and linear range of detection.

An alternative protocol is to provide anti-patient antibodies bound to the insoluble surface. After adding the sample and washing away non-specifically bound proteins, one or a combination of the test antigens are added, where the antigens are labeled, so as not to interfere with binding to the antibodies. Conveniently, fused proteins may be employed, where the peptide sequence is fused to an enzyme sequence, e.g. β-galactosidase.

It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the antigenic peptide, with a conjugate of an enzyme with an antibodies specific antibody employed as a reagent, generally added to the sample before application. Alternatively, the antigenic peptide may be conjugated to an enzyme, with antibodies specific antibody bound to the measurement region.

Thus, in one aspect, the present invention provides a method for diagnosing Celiac Sprue in an individual who has not consumed gluten for an extended period of time, such time including but not limited to one day, one week, one month, and one year prior to the performance of the diagnostic method. The advantage conferred by this aspect of the invention is that current diagnosis of a Celiac Sprue individual typically involves a preliminary diagnosis, after which the individual is placed on a gluten-free diet. If the individual's symptoms abate after initiation of the gluten-free diet, then the individual is challenged with gluten, and another diagnostic test, such as an endoscopy or T cell proliferation assay, is performed to confirm the preliminary diagnosis. This re-challenge with gluten causes extreme discomfort to the Celiac Sprue individual. One important benefit provided by certain embodiments of the invention is that such a re-challenge need not be performed to diagnose Celiac Sprue, because even very low levels of 33-mer specific antibodies and T cell responders can be identified using the methods of the invention.

In another aspect, the present invention provides a method for diagnosing Celiac Sprue by detecting the presence of a 33-mer specific antibody or a T cell responder in a bodily tissue or fluid other than intestinal mucosa. In this aspect of the invention, the diagnostic methods are performed without recourse to endoscopy or intestinal biopsy, thus avoiding the discomfort, pain, and expense attendant on such procedures in common use today.

The subject methods are useful not only for diagnosing Celiac Sprue individuals but also for determining the efficacy of prophylactic or therapeutic methods for Celiac Sprue as well as the efficacy of food preparation or treatment methods aimed at removing glutens or similar substances from food sources. Thus, a Celiac Sprue individual efficaciously treated with a prophylactic or therapeutic drug or other therapy for Celiac Sprue tests more like a non-Celiac Sprue individual with the methods of the invention. Likewise, the antibodies or T cell responders, e.g. T cell lines, of the invention that detect the toxic gluten oligopeptides of the invention are useful in detecting gluten and gluten-like substances in food and so can be used to determine whether a food treated to remove such substances has been efficaciously treated.

As used herein, the term "treating" is used to refer to both prevention of disease, and treatment of pre-existing conditions. The treatment of ongoing disease, to stabilize or improve the clinical symptoms of the patient, is of particular interest. Such treatment is desirably performed prior to loss of function in the affected tissues. Evidence of therapeutic effect may be any diminution in the severity of disease, particularly measuring the severity of such symptoms as fatigue, chronic diarrhea, malabsorption of nutrients, weight loss, abdominal distension, and anemia. Other disease indicia include the presence of antibodies specific for the 33-mer of the invention or its deamidated counterparts, glutens, antibodies specific for tissue transglutaminase or tTGase linked to the 33-mer of the invention or its deamidated counterparts, the presence of pro-inflammatory T cells and cytokines, histological examination of the villus structure of the small intestine, and the like. Patients may be adult or child, where children in particular benefit from prophylactic treatment, as prevention of early exposure to toxic gluten peptides may prevent initial development of the disease. Children suitable for prophylaxis can be identified by genetic testing for predisposition, e.g. by HLA typing; by family history, and, preferably, by the diagnostic methods of the present invention.

The various methods and reagents of the invention can be prepared and modified as described below. Although specific methods and reagents are exemplified in the discussion below, it is understood that any of a number of alternative methods, including those described above are equally applicable and suitable for use in practicing the invention. It will also be understood that an evaluation of the methods of the invention may be carried out using procedures standard in the art, including the diagnostic and assessment methods described above.

The practice of the present invention may employ conventional techniques of molecular biology (including recombinant techniques), microbiology, cell biology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction" (Mullis et al., eds., 1994); and "Current Protocols in Immunology" (J. E. Coligan et al., eds., 1991).

As noted above, the subject methods are useful to monitor the progress and efficacy of therapies to treat individuals suffering from Celiac Sprue and/or dermatitis herpetiformis. Such therapies can involve administration of an effective dose of glutenase and/or tTGase inhibitor, through a pharmaceutical formulation, incorporating glutenase into food products, administering live organisms that express glutenase, and the like. As these therapies may not have been approved by the FDA or an equivalent other regulatory agency, the methods of the invention have application in clinical trials conducted to evaluate the safety and efficacy of such therapies. Diagnosis of suitable patients may utilize a variety of criteria known to those of skill in the art in addition to those methods described herein. A quantitative increase in antibodies specific for gliadin, and/or tissue transglutaminase is indicative of the disease. Family histories and the presence of the HLA alleles HLA-DQ2 [DQ(a1*0501, b1*02)] and/or DQ8 [DQ (a1*0301, b1*0302)] are indicative of a susceptibility to the disease.

In addition to employing the diagnostic methods of the invention, the therapeutic effect may be measured in terms of clinical outcome, or may rely on immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one may look for a reduction in symptoms of a disease.

Pharmaceutical Compositions

The HLA-binding peptide inhibitors are incorporated into a variety of formulations for therapeutic administration. In one aspect, the agents are formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration can be achieved in various ways, usually by oral administration. The HLA-binding peptide inhibitors may be systemic after administration or may be localized by virtue of the formulation, or by the use of an implant that acts to retain the active dose at the site of implantation.

In pharmaceutical dosage forms, the HLA-binding peptide inhibitors may be administered in the form of their pharmaceutically acceptable salts, or they may also be used alone or in appropriate association, as well as in combination with other pharmaceutically active compounds. The agents may be combined, as previously described, to provide a cocktail of activities. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

In one embodiment of the invention, the oral formulations comprise enteric coatings, so that the active agent is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

Other enteric formulation comprise engineered polymer microspheres made of biologically erodable polymers, which display strong adhesive interactions with gastrointestinal mucus and cellular linings, can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) *J Control Release* 71(3):307-18.

Formulations are typically provided in a unit dosage form, where the term "unit dosage form," refers to physically discrete units suitable as unitary dosages for human subjects, each unit containing a predetermined quantity of glutenase calculated in an amount sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Methods of Treatment

The subject methods are used to treat individuals suffering from Celiac Sprue and/or dermatitis herpetiformis, by administering an effective dose through a pharmaceutical formulation. Diagnosis of suitable patients may utilize a variety of criteria known to those of skill in the art. A quantitative increase in antibodies specific for gliadin, and/or tissue transglutaminase is indicative of the disease. Family histories and the presence of the HLA alleles HLA-DQ2 [DQ(a1*05, b1*02)] and/or DQ8 [DQ(a1*03, b1*0302)] are indicative of a susceptibility to the disease. Specific peptide analogs may be administered therapeutically to decrease inflammation, and/or to induce antigen-specific tolerance to treat autoimmunity. Methods for the delivery of peptides that are altered from a native peptide are known in the art. Alteration of native peptides with selective changes of crucial residues can induce unresponsiveness or change the responsiveness of antigen-specific autoreactive T cells.

The therapeutic effect may be measured in terms of clinical outcome, or may rely on immunological or biochemical tests. Suppression of the deleterious T-cell activity can be measured by enumeration of reactive Th1 cells, by quantitating the release of cytokines at the sites of lesions, or using other assays for the presence of autoimmune T cells known in the art. Alternatively, one may look for a reduction in symptoms of a disease.

Various methods for administration may be employed. The dosage of the therapeutic formulation will vary widely, depending upon the nature of the disease, the frequency of administration, the manner of administration, the clearance of the agent from the host, and the like. Such treatment could either be before meals or on a once-a-day basis or on a once-a-week basis, depending on the half-life of the inhibitor. A typical dose is at least about 1 µg, usually at least about 10 µg, more usually at least about 0.1 mg, and not more than about 10 mg, usually not more than about 1 mg. Enteric coating of these peptides may also enhance their lifetimes in the gut, thereby permitting delivery to the proximal and distal small intestinal tissue. Treatment of other autoimmune disorders such as Type I diabetes with such ligands may involve oral, intravenous or intramuscular administration. The initial dose may be larger, followed by smaller maintenance doses. The dose may be administered as infrequently as weekly or biweekly, or more often fractionated into smaller doses and administered daily, with meals, semi-weekly, etc. to maintain an effective dosage level.

The HLA-binding peptide inhibitors of the invention may be administered in the treatment of Type 1 diabetes (IDDM). IDDM and celiac disease are both immunologic disorders where specific HLA alleles are associated with disease risk. Transglutaminase autoantibodies can be found in some patients with IDDM. The prevalence of transglutaminase autoantibodies is higher in diabetic patients with HLA DQ2 or DQ8.

Human type I or insulin-dependent diabetes mellitus (IDDM) is characterized by autoimmune destruction of the β cells in the pancreatic islets of Langerhans. The depletion of β cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic beta cell function. IDDM is currently treated by monitoring blood glucose levels to guide injection, or pump-based delivery, of recombinant insulin. Diet and exercise regimens contribute to achieving adequate blood glucose control. The inhibitors of the invention may be administered alone, or in combination with other therapies. The route of administration may be oral, as described for treatment of Celiac Sprue, or may be injected, e.g. i.v., i.m., etc. Administration may be performed during the pre-symptomatic phase, or in overt diabetes.

Related applications include U.S. Provisional application 60/357,238 filed Feb. 14, 2002; to U.S. Provisional Application 60/380,761 filed May 14, 2002; to U.S. Provisional Application 60/392,782 filed Jun. 28, 2002; and U.S. Provisional application No. 60/422,933, filed Oct. 31, 2002, each of which are herein specifically incorporated by reference.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Immunodominant Peptides of Gliadin are Protease Resistant

Recent studies have identified a small number of immunodominant peptides from gliadin, which account for most of the stimulatory activity of dietary gluten on intestinal and peripheral T lymphocytes found in Celiac patients. The proteolytic kinetics of these immunodominant peptides were analyzed at the small intestinal surface. Using brush border membrane vesicles from adult rat intestines, it was shown that these proline-glutamine-rich peptides are exceptionally resistant to enzymatic processing, and that dipeptidyl peptidase IV and dipeptidyl carboxypeptidase are the rate-limiting enzymes in their digestion. These results support the conclusions drawn from the tests described in Example 2 that incomplete digestion of gliadin, which results in the formation of the 33-mer oligopeptide and its deamidated counterpart formed by tTGase action, contributes to the disease symptoms of Celiac Sprue and can be employed in improved diagnostic methods for Celiac Sprue.

To dissect this complex process, liquid chromatography coupled mass spectroscopy analysis (LC-MS-MS) was utilized to investigate the pathways and associated kinetics of hydrolysis of immunodominant gliadin peptides treated with rat BBM preparations. Because the rodent is an excellent small animal model for human intestinal structure and function, rat BBM was chosen as a suitable model system for these studies.

BBM fractions were prepared from rat small intestinal mucosa as described by Ahnen et al. (1982) *J. Biol. Chem.*

257, 12129-35. Using standard assays, the specific activities of the known BB peptidases were determined to be 127 µU/µg for Aminopeptidase N (APN, EC 3.4.11.2), 60 µU/µg for dipeptidyl peptidase IV (DPP IV, EC 3.4.14.5), and 41 µU/µg for dipeptidyl carboxypeptidase (DCP, EC 3.4.15.1). No proline aminopeptidase (EC 3.4.11.5) or prolyl endopeptidase activity (PEP, EC 3.4.21.26) activity was detectable (<5 µU/µg). Alkaline phosphatase and sucrase were used as control BBM enzymes with activities of 66 µU/µg and 350 µU/µg, respectively.

BBM fractions were partially purified from the small intestinal mucosa of adult female rats maintained on an ad libitum diet of wheat-based standard rodent chow. Total protein content was determined by a modified method of Lowry with BSA as a standard. Alkaline phosphatase activity was determined with nitrophenyl phosphate. Sucrase activity was measured using a coupled glucose assay. DPP IV, proline aminopeptidase and APN were assayed continuously at 30° C. in 0.1 M Tris-HCl, pH 8.0, containing 1 mM of the p-nitroanilides ($\epsilon$=8,800 $M^{-1}$ $cm^{-1}$) Gly-Pro-pNA, Pro-pNA or Leu-pNA, the latter in additional 1% DMSO to improve solubility. DCP activity was measured in a 100 µl reaction as the release of hippuric acid from Hip-His-Leu. PEP activity was determined continuously with 0.4 mM Z-Gly-Pro-pNA in PBS: $H_2O$:dioxane (8:1.2:0.8) at 30° C. One unit is defined as the consumption of 1 µmol substrate per minute.

DPP IV and DCP are both up-regulated by a high proline content in the diet. However, APN activity using standard substrates was found to be higher than DPP IV even when fed extreme proline rich diets. Also, although a higher DCP vs. CPP activity has been observed with the model peptide Z-GPLAP at saturating concentrations, a difference in Km values could easily account the reversed ratio measured in this study. 100 µM was chosen as the initial peptide concentration, since non-saturating kinetics ($k_{cat}/K_m$) were considered to be physiologically more relevant than the maximal rates of hydrolysis ($k_{cat}$).

Proteolysis with the BBM preparation was investigated using the peptide (SEQ ID NO:1) (SEQ ID NO:1) QLQPFPQPQLPY, a product of chymotryptic digestion of α-9 gliadin (Arentz-Hansen et al. (2000) *J. Exp. Med.* 191, 603-12). This peptide has been shown to stimulate proliferation of T cells isolated from most Celiac Sprue patients, and hence is considered to possess an immunodominant epitope. It was subjected to BBM digestion, followed by LC-MS-MS analysis. A standard 50 µl digestion mixture contained 100 µM of synthetic peptide, 10 µM tryptophan and Cbz-tryptophan as internal standards, and resuspended BBM preparations with a final protein content of 27 ng/µl and exogenous proteins, as indicated, in phosphate buffered saline. After incubation at 37° C. for the indicated time, the enzymes were inactivated by heating to 95° C. for 3 minutes. The reaction mixtures were analyzed by LC-MS (SpectraSystem, ThermoFinnigan) using a C18 reversed phase column (Vydac 218TP5215, 2.1× 150 mm) with water:acetonitrile:formic acid (0.1%):trifluoroacetic acid (0.025%) as the mobile phase (flow: 0.2 ml/min) and a gradient of 10% acetonitrile for 3 minutes, 10-20% for 3 minutes, 20-25% for 21 minutes followed by a 95% wash. Peptide fragments in the mass range of m/z=300-2000 were detected by electrospray ionization mass spectroscopy using a LCQ ion trap, and their identities were confirmed by MSMS fragmentation patterns.

While the parent peptide (SEQ ID NO:1) QLQPFPQPQLPY disappeared with an apparent half time of 35 min, several intermediates were observed to accumulate over prolonged periods (FIG. 1A). The MS intensities (m/z=300-2000 g/mol) and $UV_{280}$ absorbances of the parent peptides (SEQ ID NO:1) QLQPFPQPQLPY and (SEQ ID NO:3) PQPQLPYPQPQLPY were found to depend linearly on concentration in the range of 6-100 µM. The reference peptides (SEQ ID NO:4) PQPQLPYPQPQLP, (SEQ ID NO:5) QLQPFPQPQLP, (SEQ ID NO:6) QPQFPQPQLPY and (SEQ ID NO:7) QPFPQPQLP were generated individually by limited proteolysis of the parent peptides with 10 µg/ml carboxypeptidase A (C-0261, Sigma) and/or 5.9 µg/ml leucine aminopeptidase (L-5006, Sigma) for 160 min. at 37° C. and analyzed by LC-MS as in FIG. 1.

Indeed, the subsequent processing of the peptide was substantially retarded (FIG. 1B). The identities of the major intermediates were confirmed by tandem MS, and suggested an unusually high degree of stability of the (SEQ ID NO:8) PQPQLP sequence, a common motif in T cell stimulating peptides. Based on this data and the known amino acid preferences of the BBM peptidases, the digestive breakdown of (SEQ ID NO:1) QLQPFPQPQLPY was reconstructed, as shown in the insert of FIG. 1B. The preferred pathway involves serial cleavage of the N-terminal glutamine and leucine residues by aminopeptidase N (APN), followed by removal of the C-terminal tyrosine by carboxypeptidase P (CPP) and hydrolysis of the remaining N-terminal QP-dipeptide by DPP IV. As seen in FIG. 1B, the intermediate (SEQ ID NO:6) QPFPQPQLPY (formed by APN attack on the first two N-terminal residues) and its derivatives are increasingly resistant to further hydrolysis. Because the high proline content seemed to be a major cause for this proteolytic resistance, digestion was compared with a commercially available non-proline control peptide (SEQ ID NO:9) RRLIEDNEYTARG (Sigma, St. Louis, Mo.). Initial hydrolysis was much faster ($t_{1/2}$=10 min). More importantly, digestive intermediates were only transiently observed and cleared completely within one hour, reflecting a continuing high specificity of the BBM for the intermediate peptides.

Because the three major intermediate products (SEQ ID NO:6) QPFPQPQLPY, (SEQ ID NO:7) QPFPQPQLP, (SEQ ID NO:11) FPQPQLP) observed during BBM mediated digestion of (SEQ ID NO:1) QLQPFPQPQLPY are substrates for DPP IV, the experiment was repeated in the presence of a 6-fold excess activity of exogenous fungal DPP IV. Whereas the relatively rapid decrease of the parent peptide and the intermediate levels of (SEQ ID NO:5) QLQPFPQPQLP were largely unchanged, the accumulation of DPP IV substrates was entirely suppressed and complete digestion was observed within four hours. (FIG. 1B, open bars).

To investigate the rate-limiting steps in BBM mediated digestion of gliadin peptides from the C-terminal end, another known immunodominant peptide derived from wheat α-gliadin, (SEQ ID NO:3) PQPQLPYPQPQLPY, was used. Although peptides with N-terminal proline residues are unlikely to form in the small intestine (none were observed during BBM digestion of (SEQ ID NO:1) QLQPFPQPQLPY, FIG. 1A), they serve as a useful model for the analysis of C-terminal processing since the N-terminal end of this peptide can be considered proteolytically inaccessible due to minimal proline aminopeptidase activity in the BBM. As shown in FIG. 2, this peptide is even more stable than (SEQ ID NO:1) QLQPFPQPQLPY. In particular, removal of the C-terminal tyrosine residue by carboxypeptidase P (CPP) is the first event in its breakdown, and more than four times slower than APN activity on (SEQ ID NO:1) QLQPFPQPQLPY (FIG. 1B). The DCP substrate (SEQ ID NO:4) PQPQLPYPQPQLP emerges as a major intermediate following carboxypeptidase P catalysis, and is highly resistant to further digestion, presumably due to the low level of endogenous DCP activity naturally associated with the BBM. To confirm the role of DCP as a rate-limiting enzyme in the C-terminal processing of immunodominant gliadin peptides, the reaction mixtures were supplemented with rabbit lung DCP. Exogenous DCP significantly reduced the accumulation of (SEQ ID NO:4) PQPQLPYPQPQLP after overnight incubation in a dose dependent manner (FIG. 2C). Conversely, the amount of accumulated (SEQ ID NO:4) PQPQLPYPQPQLP increased more than 2-fold in the presence of 10 µM of captopril, a DCP-specific inhibitor, as compared with unsupplemented BBM.

Together, the above results demonstrate that (i) immunodominant gliadin peptides are exceptionally stable toward breakdown catalyzed by BBM peptidases, and (ii) DPP IV and especially DCP are rate-limiting steps in this breakdown process at the N- and C-terminal ends of the peptides, respectively. Because BBM exopeptidases are restricted to N- or C-terminal processing, it was investigated if generation of additional free peptide ends by pancreatic enzymes would accelerate digestion. Of the pancreatic proteases tested, only elastase at a high (non-physiological) concentration of 100 ng/µl was capable of hydrolyzing (SEQ ID NO:3) PQPQLPYPQPQ↓LPY. No proteolysis was detected with trypsin or chymotrypsin.

The above data demonstrates that proline-rich gliadin peptides are extraordinarily resistant to digestion by small intestinal endo- and exopeptidases, and therefore are likely to accumulate at high concentrations in the intestinal cavity after a gluten rich meal. The pathological implication of digestive resistance is strengthened by the observed close correlation of proline content and celiac toxicity as observed in the various common cereals (Schuppan (2000) *Gastroenterology* 119, 234-42).

EXAMPLE 2

Immunodominant Peptide of Wheat Gliadin

It has long been known that the principal toxic components of wheat gluten are a family of closely related Pro-Gln rich proteins called gliadins. Recent reports have suggested that peptides from a short segment of α-gliadin appear to account for most of the gluten-specific recognition by CD4+ T cells from Celiac Sprue patients. These peptides are substrates of tissue transglutaminase (tTGase), the primary auto-antigen in Celiac Sprue, and the products of this enzymatic reaction bind to the class II HLA DQ2 molecule. This example demonstrates, using a combination of in vitro and in vivo animal and human studies, that this "immunodominant" region of α-gliadin is part of an unusually long proteolytic product generated by the digestive process that: (a) is exceptionally resistant to further breakdown by gastric, pancreatic and intestinal brush border proteases; (b) is the highest specificity substrate of human tissue transglutaminase (tTGase) discovered to date; (c) contains at least six overlapping copies of epitopes known to be recognized by patient derived T cells; (d) stimulates representative T cell clones that recognize these epitopes with sub-micromolar efficacy; and (e) has homologs in proteins from all toxic foodgrains but no homologs in non-toxic foodgrain proteins. In aggregate, these findings demonstrate that the onset of symptoms upon gluten exposure can be traced back to a small segment of α-gliadin. Finally, it is shown that this "super-antigenic" long peptide can be detoxified in vitro and in vivo by treatment with bacterial prolyl endopeptidase, providing a strategy for peptidase therapy for Celiac Sprue.

Identification of stable peptides from gastric protease, pancreatic protease and brush border membrane peptidase catalyzed digestion of recombinant α2-gliadin: α2-gliadin, a representative α-gliadin (Arentz-Hansen et al. (2000) Gut 46:46), was expressed in recombinant form and purified from *E. coli*. The α2-gliadin gene was cloned in pET28a plasmid (Novagen) and transformed into the expression host BL21 (DE3) (Novagen). The transformed cells were grown in 1-liter cultures of LB media containing 50 µg/ml of kanamycin at 37° C. until the OD600 0.6-1 was achieved. The expression of α2-gliadin protein was induced with the addition of 0.4 mM isopropyl β-D-thiogalactoside (Sigma), and the cultures were further incubated at 37° C. for 20 hours. The cells expressing the recombinant α2-gliadin were centrifuged at 3600 rpm for 30 minutes. The pellet was resuspended in 15 ml of disruption buffer (200 mM sodium phosphate; 200 mM NaCl; 2.5 mM DTT; 1.5 mM benzamidine; 2.5 mM EDTA; 2 mg/L pepstatin; 2 mg/L leupeptin; 30% v/v glycerol) and lysed by sonication (1 minute; output control set to 6). After centrifugation at 45000 g for 45 min, the supernatant was discarded and the pellet containing gliadin protein was resuspended in 50 ml of 7M urea in 50 mM Tris (pH=8.0). The suspension was again centrifuged at 45000 g for 45 min and the supernatant was harvested for purification.

The supernatant containing α2-gliadin was incubated with 1 ml of nickel-nitrilotriacetic acid resin (Ni-NTA; Qiagen) overnight and then batch-loaded on a column with 2 ml of Ni-NTA. The column was washed with 7 M urea in 50 mM Tris (pH=8.0), and α2-gliadin was eluted with 200 mM imidazole, 7 M urea in 50 mM Tris (pH=4.5). The fractions containing α2-gliadin were pooled into a final concentration of 70% ethanol solution, and two volumes of 1.5 M NaCl were added to precipitate the protein. The solution was incubated at 4° C. overnight, and the final precipitate was collected by centrifugation at 45000 g for 30 min., rinsed in water, and re-centrifuged to remove the urea. The final purification step of the α-2 gliadin was developed with reverse-phase HPLC. The Ni-NTA purified protein fractions were pooled in 7 M urea buffer and injected to a Vydac (Hesperia, Calif.) polystyrene reverse-phase column (i.d. 4.6 mm×25 cm) with the starting solvent (30% of solvent B: 1:1 HPLC-grade acetonitrile/isopropanol: 0.1% TFA). Solvent A was an aqueous solution with 0.1% TFA. The separation gradient extended from 30-100% of solvent B over 120 min. at a flow rate of 0.8 ml/min.

TABLE 2

| | Amount of Peptides Digested after 15 hours | | |
|---|---|---|---|
| | 33-mer | Control A | Control B |
| H1P0 | <20% | >90% | >90% |
| H2P0 | <20% | >61% | >85% |
| H3P0 | <20% | >87% | >95% |
| H4P0 | <20% | >96% | >95% |
| H5P0 | <20% | >96% | >95% |

The purity of the recombinant gliadin was >95%, which allowed for facile identification and assignment of proteolytic products by LC-MS/MS/UV. Although many previous studies utilized pepsin/trypsin treated gliadins, it was found that, among gastric and pancreatic proteases, chymotrypsin played a major role in the breakdown of α2-gliadin, resulting in many small peptides from the C-terminal half of the protein and a few longer (>8 residues) peptides from the N-terminal half, the most noteworthy being a relatively large fragment, the 33-mer (SEQ ID NO:12) LQLQPF-PQPQLPYPQPQLPYPQPQLPYPQPQPF (residues 57-89). This peptide was of particular interest for two reasons: (a)

whereas most other relatively stable proteolytic fragments were cleaved to smaller fragments when the reaction times were extended, the 33-mer peptide remained intact despite prolonged exposure to proteases; and (b) three distinct patient-specific T cell epitopes identified previously are present in this peptide, namely, SEQ ID NO:59 PFPQPQLPY, SEQ ID NO:60 PQPQLPYPQ (3 copies), and SEQ ID NO:61 PYPQPQLPY (2 copies).

Figure 4:
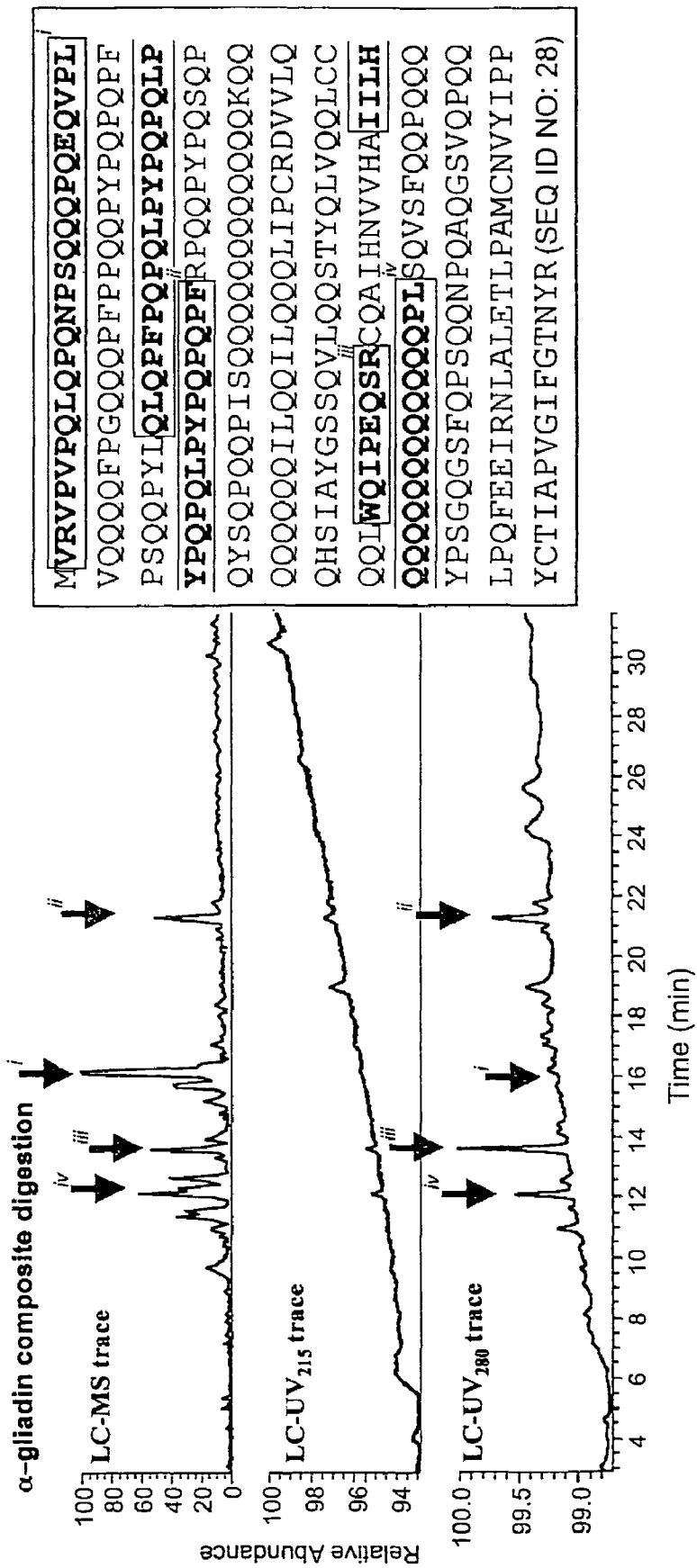
FIG. 4. Products of gastric and pancreatic protease mediated digestion of α2-gliadin under physiological conditions. Analysis was performed by LC-MS. The longest peptides are highlighted by arrows and also in the sequence of α2-gliadin (inset).
Figure 5:
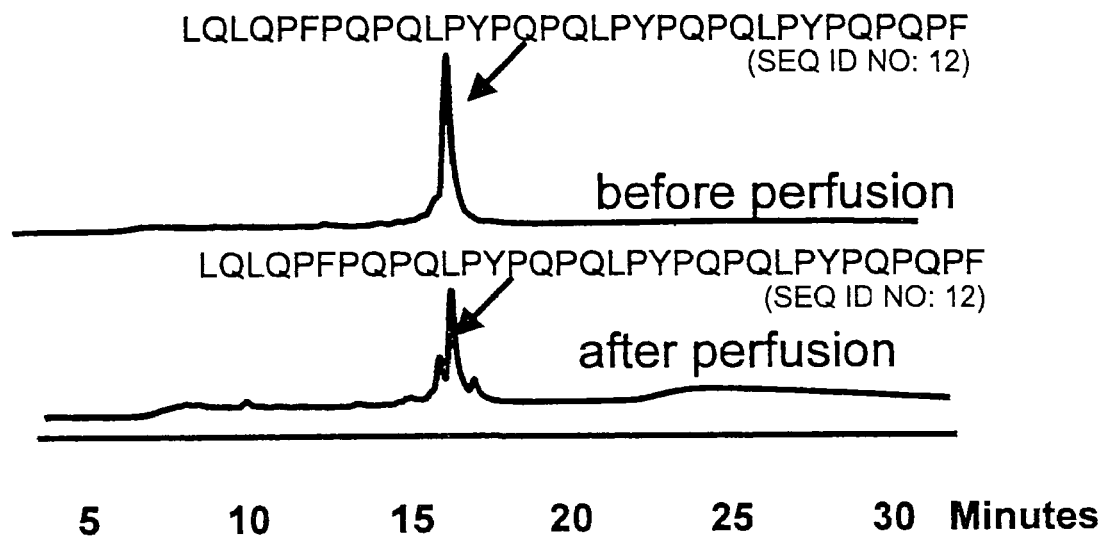
FIG. 5. In vivo brush border membrane digestion of peptides. $LC-UV_{215}$ traces of 25 µM of (SEQ ID NO:12) LQLQPFPQPQLPYPQPQLPYPQPQLPYPQPQPF before perfusion and after perfusion (residence time=20 min). $LC-UV_{215}$ traces of 50 µM of (SEQ ID NO:1) QLQPFPQPQLPY before perfusion and after perfusion (residence time=20 min).
Figure 5:
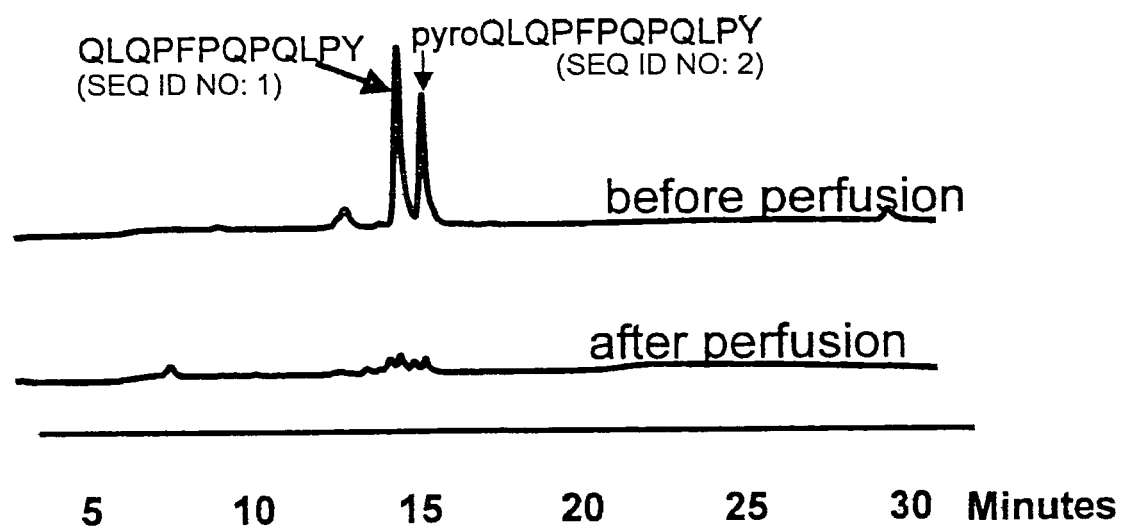

To establish the physiological relevance of this peptide, composite gastric/pancreatic enzymatic digestion of α2 gliadin was then examined. As expected, enzymatic digestion with pepsin (1:100 w/w ratio), trypsin (1:100), chymotrypsin (1:100), elastase (1:500) and carboxypeptidase (1:100) was quite efficient, leaving behind only a few peptides longer than 9 residues (the minimum size for a peptide to show class II MHC mediated antigenicity) (FIG. 4). In addition to the above-mentioned 33-mer, the peptide (SEQ ID NO:10) WQIPEQSR was also identified, and was used as a control in many of the following studies. The stability of the 33-mer peptide can also be appreciated, when comparing the results of a similar experiment using myoglobin (another common dietary protein). Under similar proteolytic conditions, myoglobin is rapidly broken down into much smaller products. No long intermediate is observed to accumulate.

The small intestinal brush-border membrane (BBM) enzymes are known to be vital for breaking down any remaining peptides from gastric/pancreatic digestion into amino acids, dipeptides or tripeptides for nutritional uptake. Therefore a comprehensive analysis of gliadin metabolism also required investigations into BBM processing of gliadin peptides of reasonable length derived from gastric and pancreatic protease treatment. BBM fractions were prepared from rat small intestinal mucosa. The specific activities of known BBM peptidases were verified to be within the previously reported range. Whereas the half-life of disappearance of (SEQ ID NO:10) WQIPEQSR was ~60 min. in the presence of 12 ng/µl BBM protein, the half-life of (SEQ ID NO:12) LQLQPFPQPQLPYPQPQLPYPQPQLPYPQPQPF digestion was >20 h. Therefore, the latter peptide remains intact throughout the digestive process in the stomach and upper small intestine, and is poised to act as a potential antigen for T cell proliferation and intestinal toxicity in genetically susceptible individuals.

Verification of proteolytic resistance of the 33-mer gliadin peptide with brush border membrane preparations from human intestinal biopsies: To validate the above conclusions, derived from studies with rat BBM preparations, in the context of human intestinal digestion, BBM preparations were prepared from a panel of adult human volunteers, one of whom was a Celiac Sprue patient in remission, while the rest were found to have normal intestinal histology. (SEQ ID NO:12) LQLQPFPQPQLPYPQPQLPYPQPQLPYPQPQPF, (SEQ ID NO:1) QLQPFPQPQLPY (an internal sequence from the 33-mer used as a control), (SEQ ID NO:10) WQIPEQSR and other control peptides (100 µM) were incubated with BBM prepared from each human biopsy (final aminopeptidase N activity of 13 µU/µl) at 37° C. for varying time periods. While (SEQ ID NO:1) QLQPFPQPQLPY, (SEQ ID NO:10) WQIPEQSR and other control peptides were completely proteolyzed within 1-5 h, the long peptide remained largely intact for at 19 hours. These results confirm the equivalence between the rat and human BBM for the purpose of this study.

Verification of proteolytic resistance of the 33-mer gliadin peptide in intact animals: The proteolytic resistance of the 33-mer gliadin peptide, observed in vitro using BBM from rats and humans, was confirmed in vivo using a perfusion protocol in intact adult rats (Smithson and Gray (1977) *J. Clin. Invest.* 60:665). Purified peptide solutions were perfused through a 15-20 cm segment of jejunum in a sedated rat with a residence time of 20 min., and the products were collected and subjected to LC-MS analysis. Whereas >90% of (SEQ ID NO:1) QLQPFPQPQLPY was proteolyzed in the perfusion experiment, most of the 33-mer gliadin peptide remained intact. These results demonstrate that the 33-mer peptide is very stable as it is transported through the mammalian upper small intestine.

The 33-mer gliadin peptide is an excellent substrate for tGase, and the resulting product is a highly potent activator of patient-derived T cells. A number of recent studies have demonstrated that regiospecific deamidation of immunogenic gliadin peptides by tGase increases their affinity for HLA-DQ2 as well as the potency with which they activate patient-derived gluten-specific T cells. It has been shown the specificity of tGase for certain short antigenic peptides derived from gliadin is higher than its specificity toward its physiological target site in fibronectin, for example, the specificity of tGase for the α-gliadin derived peptide (SEQ ID NO: 3) PQPQLPYPQPQLPY is 5-fold higher than that for its target peptide sequence in fibrinogen, its natural substrate. The kinetics and regiospecificity of deamidation of the 33-mer α-gliadin peptide identified as above were therefore measured. The $k_{cat}/K_M$ was higher than that reported for any peptide studied thus far: kcat/KM=440 min-1 mM-1 for (SEQ ID NO:12) LQLQPFPQPQLPYPQPQLPYPQPQLPYPQPQPF compared to kcat/KM=82 min-1 mM-1 for PQPQLPY and kcat/KM=350 min-1 mM-1 for (SEQ ID NO: 3) PQPQLPYPQPQLPY.

Moreover, LC-MS-MS analysis revealed that (SEQ ID NO:12) LQLQPFPQPQLPYPQPQLPYPQPQLPYPQPQPF was selectively deamidated by tGase at the underlined residues. Since tGase activity is associated with the brush border membrane of intestinal enterocytes, it is likely that dietary uptake of even small quantities of wheat gluten will lead to the build-up of sufficient quantities of this 33-mer gliadin peptide in the intestinal lumen so as to be recognized and processed by tGase.

Figure 6:
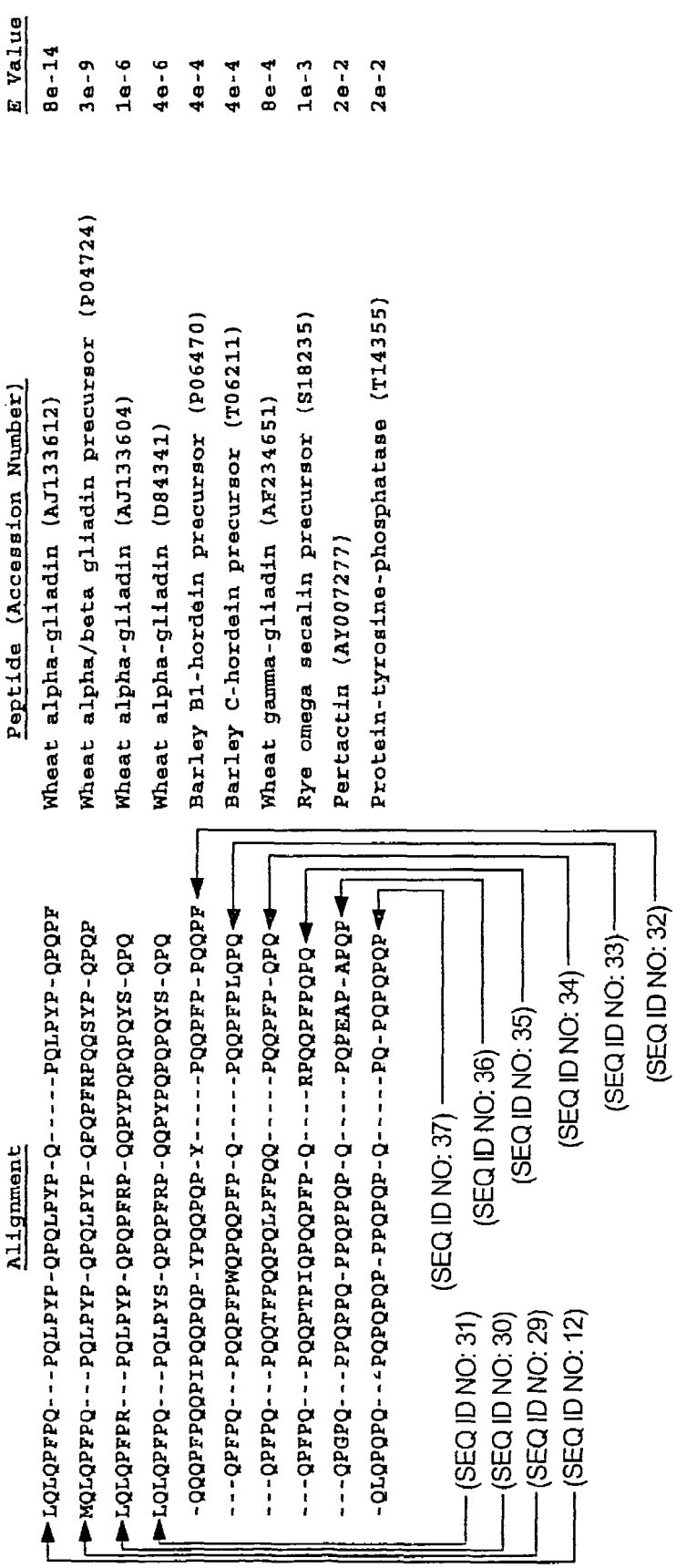
FIG. 6. Alignment of representative gluten and non-gluten peptides homologous to (SEQ ID NO:12) LQLQPFPQPQLPYPQPQLPYPQPQLPYPQPQPF.
Figure 7:
FIG. 7. Breakdown and detoxification of 33-mer gliadin peptide with PEP. In vitro incubation of PEP (540 mU/ml) with the 33-mer gliadin peptide (100 µM) for the indicated time. In vivo digestion of the 33-mer gliadin peptide (25 µM) with PEP (25 mU/ml) and the rat's intestine (residence time=20 min).
Figure 7:
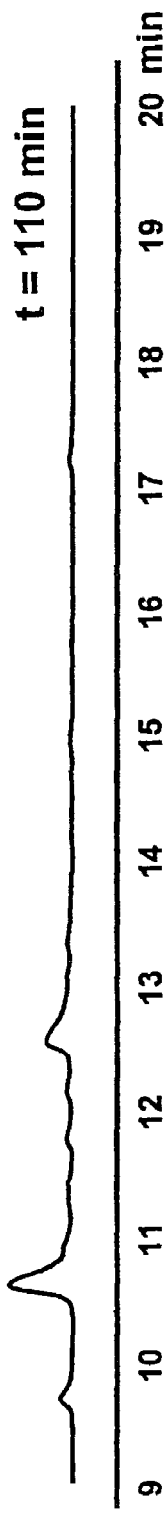
Figure 7:
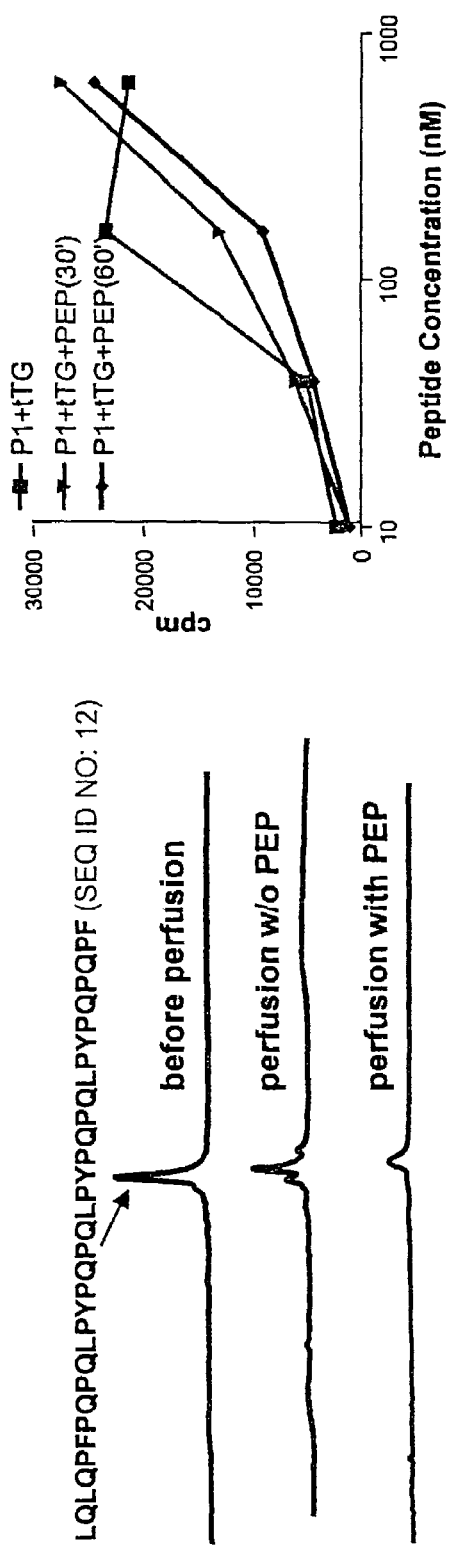

Structural characteristics of the 33-mer gliadin peptide and its naturally occurring homologs: Sequence alignment searches using BLASTP in all non-redundant protein databases revealed several homologs (E-value <0.001) of the 33-mer gliadin peptide. Interestingly, foodgrain derived homologs were only found in gliadins (from wheat), hordeins (from barley) and secalins (from rye), all of which have been proven to be toxic to Celiac patients. See FIG. 6. Nontoxic foodgrain proteins, such as avenins (in oats), rice and maize, do not contain homologous sequences to the 33-mer gliadin. In contrast, a BLASTP search with the entire α2-gliadin sequence identified foodgrain protein homologs from both toxic and nontoxic proteins. Based on available information regarding the substrate specificities of gastric, pancreatic and BBM proteases and peptidases, it is predicted that, although most gluten homologs to the 33-mer gliadin peptide contained multiple proteolytic sites and are therefore unlikely to be completely stable toward digestion, several sequences from wheat, rye and barley are expected to be comparably resistant to gastric and intestinal proteolysis. The stable peptide homologs to the 33-mer α2-gliadin peptide are (SEQ ID NO:13) QPQPFPPQLPYPQTQPFPPQQPYPQPQPQYPQPQ (from α1- and α6-gliadins); (SEQ ID NO:14) QQQPFPQQPIPQQPQPYPQQPQPYPQQPFPPQQPF (from B1 hordein); (SEQ ID NO:15) QPFPQPQQTFPQQPQLPFPQQPQQPFPQPQ (from γ-gliadin); (SEQ ID NO:16) QPF- PQPQQPTPIQPQQPFPQRPQQPFPQPQ (from ω-secalin). These stable peptides are all located at the N-terminal region of the corresponding proteins. The presence of proline residues after otherwise cleavable residues in these peptides would contribute to their proteolytic stability.

The unique primary sequence of the 33-mer gliadin peptide also had homologs among a few non-gluten proteins. Among the strongest homologs were internal sequences from pertactin (a highly immunogenic protein from *Bordetella pertussis*) and a mammalian inositol-polyphosphate 5-phosphatase of unknown function. In both cases available information suggested that the homology could have biologically relevance. For example, the region of pertactin that is homologous to the 33-mer gliadin peptide is known to be part of the immunodominant segment of the protein. In the case of the homologous phosphatase, the corresponding peptide region of the phosphatase is known to be responsible for vesicular trafficking of the phosphatase to the cytoplasmic Golgi. In analogy with the current picture of how gliadin peptides are presented to HLA-DQ2 via a tTGase mediated pathway, these Pro-Gln-rich segments of both pertactin and the phosphatase are likely to be good tTGase substrates. To test this hypothesis, the corresponding peptides were synthesized, and the selectivity of tTGase for these peptides was measured. As predicted, both peptides were found to be good substrates of tTGase. The tTGase enzyme plays a central role in receptor mediated endocytosis of several biologically important proteins. The biological activities of both pertactin and the phosphatase may depend on tTGase mediated trafficking.

Secondary structural studies using circular dichroism spectroscopy on the 33-mer gliadin peptide as well as its homologs from pertactin and the inositol-polyphosphate 5-phosphatase demonstrate that these peptides have strong type II polyproline helical character. In addition to reinforcing the proteolytic resistance of these peptides, the type II polyproline helical conformation is also likely to enhance their affinity for class II MHC proteins.

Although gluten proteins from foodgrains such as wheat, rye and barley are central components of a nutritious diet, they can be extremely toxic for patients suffering from Celiac Sprue. To elucidate the structural basis of gluten toxicity in Celiac Sprue, comprehensive proteolytic analysis was performed on a representative recombinant gliadin under physiologically relevant conditions. An unusually long and proteolytically stable peptide product was discovered, whose physiological relevance was confirmed by studies involving brush border membrane proteins from rat and human intestines as well as intestinal perfusion assays in live rats. In aggregate, these data demonstrate that this peptide and its homologs found in other wheat, rye and barley proteins are the "root cause" of the initial inflammatory response to dietary wheat in Celiac Sprue patients in remission.

EXAMPLE 3

Human leukocyte antigen DQ2 is a class II major histocompatibility complex protein that plays a critical role in the pathogenesis of Celiac Sprue by binding to epitopes derived from dietary gluten and triggering the inflammatory response of disease-specific T cells. Inhibition of DQ2 mediated antigen presentation in the small intestinal mucosa of Celiac Sprue patients therefore represents a potentially attractive mode of therapy for this widespread but unmet medical need. Starting from a pro-inflammatory, proteolytically resistant, 33-residue peptide, (SEQ ID NO:12) LQLQPFPQPEL PYPQPELPYPQPELPYPQPQPF, we embarked upon a systematic effort to dissect the relationships between peptide structure and DQ2 affinity, and to translate these insights into prototypical DQ2 blocking agents. Three structural determinants within the first 20 residues of this 33-mer peptide, including a (SEQ ID NO: 18) PQPELPYPQ epitope, its N-terminal flanking sequence and a downstream Glu residue, were found to be critical for DQ2 recognition. Guided by the X-ray crystal structure of DQ2, the L11 and L18 residues in the truncated 20-mer analogue were replaced with sterically bulky groups so as to retain high DQ2 affinity but abrogate T cell recognition. A dimeric ligand synthesized by regiospecific coupling of the 20-mer peptide with a bifunctional linker, was identified as an especially potent DQ2 binding agent. Two such ligands were able to attenuate the proliferation of disease-specific T cell lines in response to gluten antigens, and therefore represent prototypical examples of pharmacologically suitable DQ2 blocking agents for the potential treatment of Celiac Sprue.

Inhibition of antigen presentation by blocking a disease-specific MHC on antigen presenting cells with peptide (and occasionally non-peptide) ligands has been previously explored as a therapeutic strategy for autoimmune diseases such as multiple sclerosis, rheumatoid arthritis, diabetes, and experimental autoimmune encephalomyelitis. Such therapy is of particular interest for the treatment of Celiac Sprue. First, to date no non-dietary treatment has been developed for this widespread, lifelong disease; as such, there is an acute unmet need. Second, in contrast to the organs affected by most other autoimmune diseases, the small intestine is readily accessible via oral administration of a therapeutic candidate. Finally, and perhaps most importantly, among HLA mediated diseases, Celiac Sprue is unique in that an environmental trigger (dietary gluten) has been identified and extensively dissected at an immunological level. In turn, these studies have led to the identification of proteolytically resistant gluten peptides that are generated by physiological processes and are efficiently presented to disease associated T cells in a DQ2 restricted fashion. Thus, if these naturally occurring T cell stimulatory agents can be transformed into inhibitors of DQ2 mediated antigen presentation, they can be considered as appropriate medicinal leads for Celiac Sprue.

A Pro- and Gln-rich 33-mer peptide from α2-gliadin, (SEQ ID NO:12) LQLQPFPQPELPYPQPELPYPQPQPF (transglutaminase-catalyzed Gln->Glu changes underlined), is a particularly interesting lead peptide for this purpose. Its extreme resistance to breakdown by luminal proteases and intestinal brush-border enzymes allows it to persist for a considerable duration in the upper small intestine, the primary affected region of the gastrointestinal tract in a Celiac Sprue patient. Not only does this peptide have a high affinity for HLA-DQ2, it is displayed on the surface of antigen presenting cells with unusual robustness. Not surprisingly, it is a potent proliferative trigger of gluten-responsive T cells from small intestinal biopsy samples of all DQ2 Celiac Sprue patients tested thus far. Although this peptide is multivalent (it has 6 overlapping copies of 3 epitopes), it binds to HLA-DQ2 with a 1:1 stoichiometry. It has a considerably higher affinity for DQ2 than any of its constituent epitopes (SEQ ID NO:17) PFPQPELPY, (SEQ ID NO:18) PQPELPYPQ and (SEQ ID NO:58) PYPQPELPY. Together, these observations led us to hypothesize that the 33-mer peptide harbors secondary interactions with DQ2 outside the core antigen binding pocket. Understanding the precise nature of these interactions would therefore be a critical prerequisite for exploiting its potential as a medicinal lead in the design of DQ2 blocking agents.

In this report we have dissected the structural determinants of the high-affinity interaction between the 33-mer peptide and HLA-DQ2. Based on these findings, we designed and synthesized simple analogues of the 33-mer peptide that retain its strong affinity for DQ2 but are not recognized by 33-mer responsive T cells from Celiac biopsies. The ability of these putative blocking agents to inhibit T cell proliferation in response to gluten antigens was also demonstrated. These peptides represent the first prototypical examples of pharmacologically relevant DQ2 blocking agents for potential treatment of Celiac Sprue.

Experimental Section

DQ2 expression and purification. Soluble DQ2 molecules were expressed and purified as previously described. Briefly, the soluble extracellular domains of the DQ2 α and β chains were co-expressed in High Five insect cells using a pAcAB3 baculovirus expression system, and were affinity-purified using the anti-DQ2 mAb 2.12.E11. The sequence (SEQ ID NO:55) QLQPFPQPELPY was fused to the N-terminus of the DQ2 β-chain by a 15-residue linker (SEQ ID NO:56) (GAGSLVPRGSGGGGS), which includes a thrombin site. A complementary Fos/Jun leucine zipper pair was engineered at the C-terminal ends of α and β chains, respectively, with intervening factor Xa proteolysis sites, to increase the heterodimer stability during protein expression.

The concentration of HLA-DQ2 was determined by UV spectrophotometry at 280 nm using the absorption coefficient factor 75,700 $cm^{-1}M^{-1}$ as calculated from the contents of tyrosine, tryptophan and cystine in the DQ2 sequence (22). Prior to use in binding experiments with exogenous ligands, the DQ2-ligand fusion protein was first treated with ~2% w/w thrombin in pH 7.3 PBS at 0° C. for 2 h.

Peptide synthesis, labeling and purification. All peptides used in this study were synthesized using Boc/HBTU chemistry starting from N-α-t-Boc-L-aminoacyl-phenylacetamidomethyl (PAM) resin. Peptides were labeled at their N-termini while still attached to the resin with 5- (and 6-) carboxyfluorescein, 1-(3-Dimethylaminopropyl)-3-ethyl-carbodiimide hydrochloride (EDC-HCl), and 1-Hydroxy-7-azabenzotriazole (HOAt) in 1:1:1 ratio in dimethylformamide as the solvent. Following cleavage of the peptidyl resin in trifluoroacetic acid/trifluoromethanesulfonic acid/thioanisole (TFA/TFMSA/thioanisole 10:1:1, v/v/v) for 4 h, the crude peptides were precipitated in cold ether and dissolved in 1:1 v/v acetonitrile/water. The peptides were purified by reverse-phase HPLC on a semi-preparative $C_{18}$ column using a water-acetonitrile gradient in 0.1% (v/v) TFA. The identity and purity of the peptides were confirmed by electrospray mass spectrometry and analytical reverse-phase HPLC. The peptides were lyophilized and stored at −20° C. Prior to use, peptide stock solutions were prepared in 10 mM PBS with 0.02% sodium azide, and their concentrations were determined by UV-Vis spectrophotometry at 495 nm using the absorption coefficient factor 80,200 $cm^{-1}M^{-1}$ for the fluorescein-labeled peptide. The integrity of the peptide stocks was monitored by analytical HPLC every several months.

Figure 10:
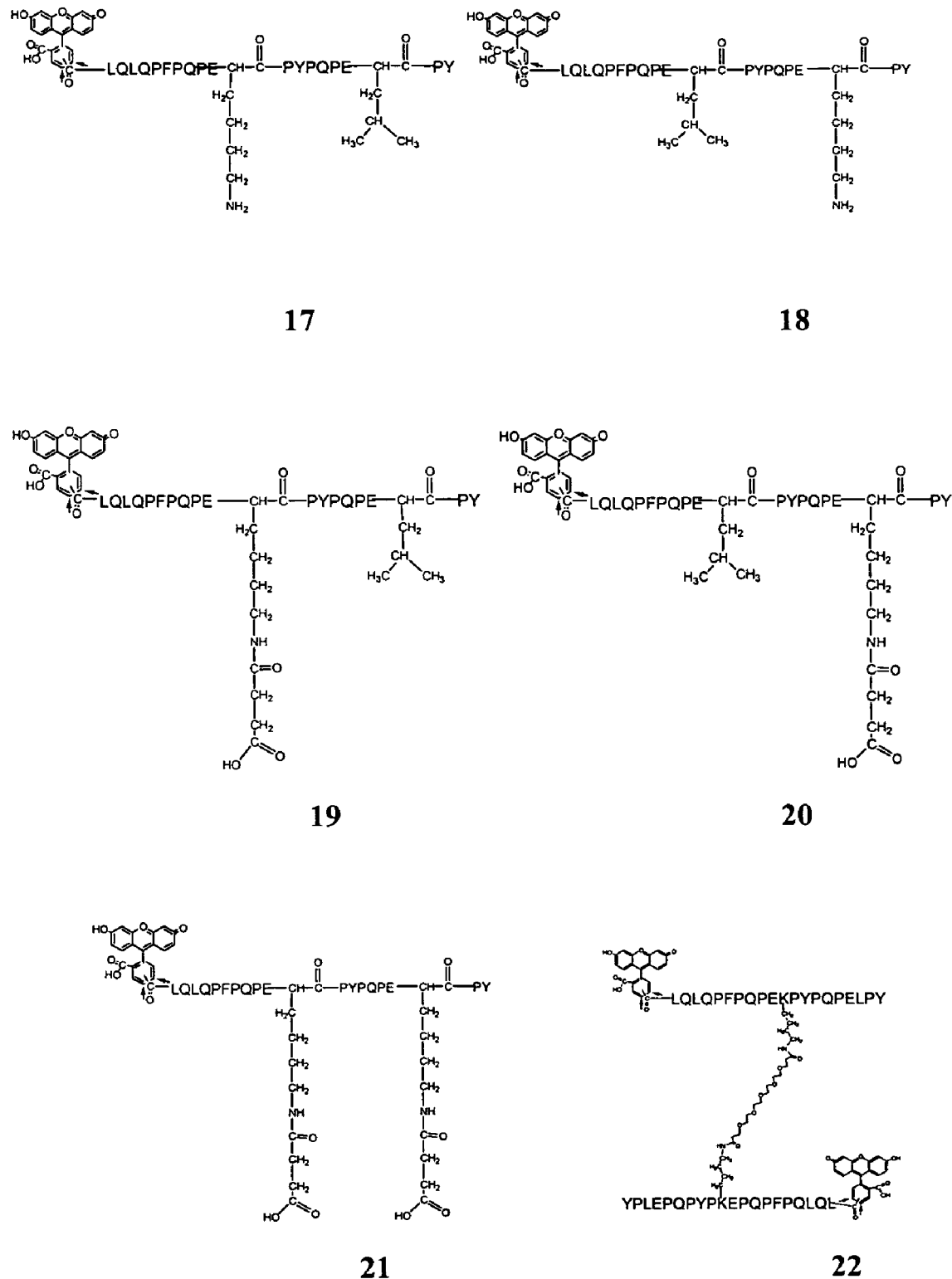
FIG. 10. Structures of candidate DQ2 blocking agents 19-22.
Figure 11:
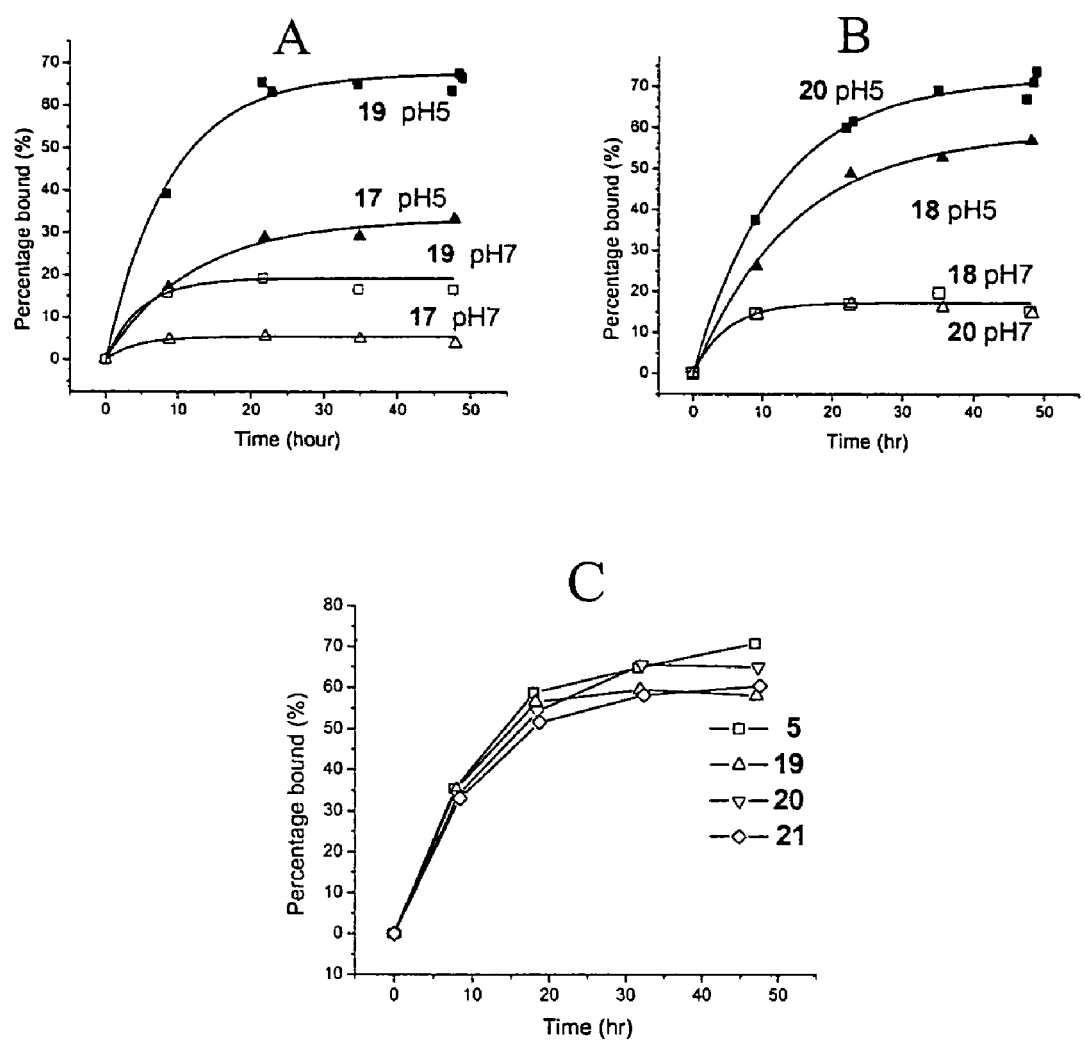
FIG. 11A-11C. Kinetic analysis of exchange of compounds 17-21 in the DQ2 binding pocket. (A) Exchange of compounds 17 (Δ) and 19 ( ) onto DQ2 at pH 5.5 (filled circles) and pH 7.3 (open circles). (B) Exchange of compounds 18 (Δ) and 20 ( ) onto DQ2 at pH 5.5 (filled circles) and pH 7.3 (open circles). (C) Comparative kinetics of DQ2 binding of compounds 5 ( ), 19 (Δ), 20 (∇), and 21(◇) at pH 5.5 and 37° C.
Figure 12:
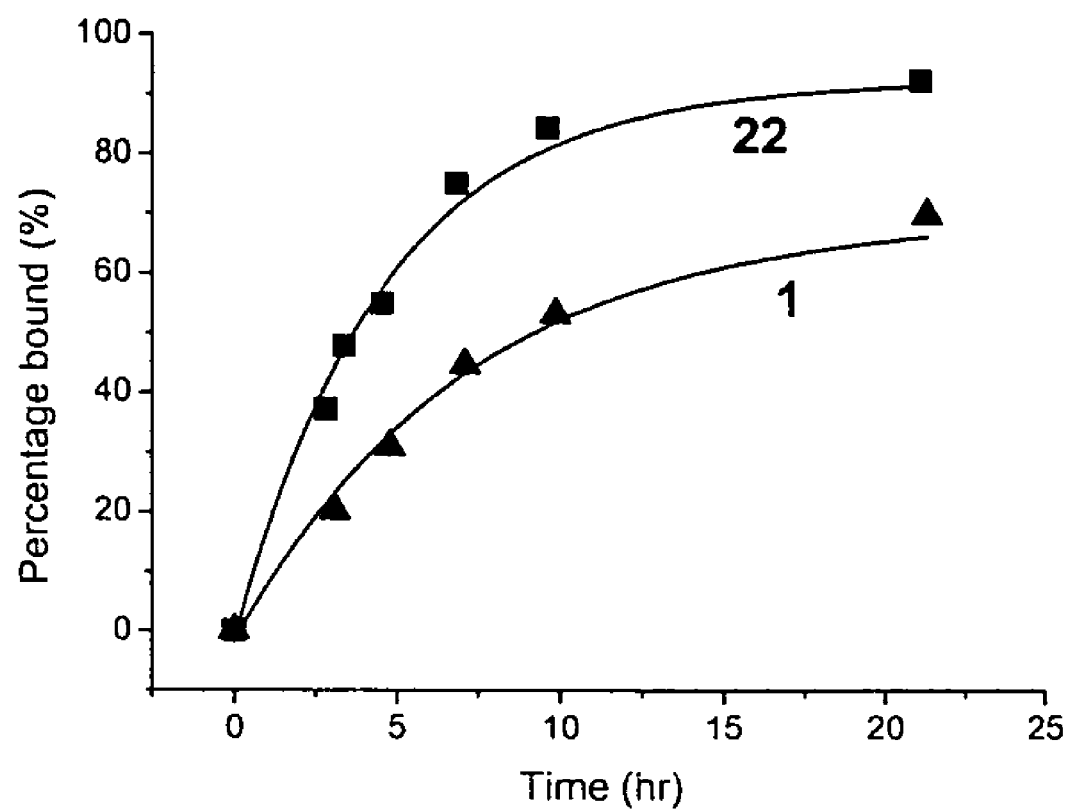
FIG. 12. Kinetic analysis of exchange of compound 22 (filled) and 33-mer 1 (filled Δ) at pH 5.5. Data at pH 7.3 was similar; at this pH peptide 1 reaches a maximum occupancy of 28% (45 h), whereas peptide 22 reaches a maximum occupancy of 40% (20 h).
Figure 13:
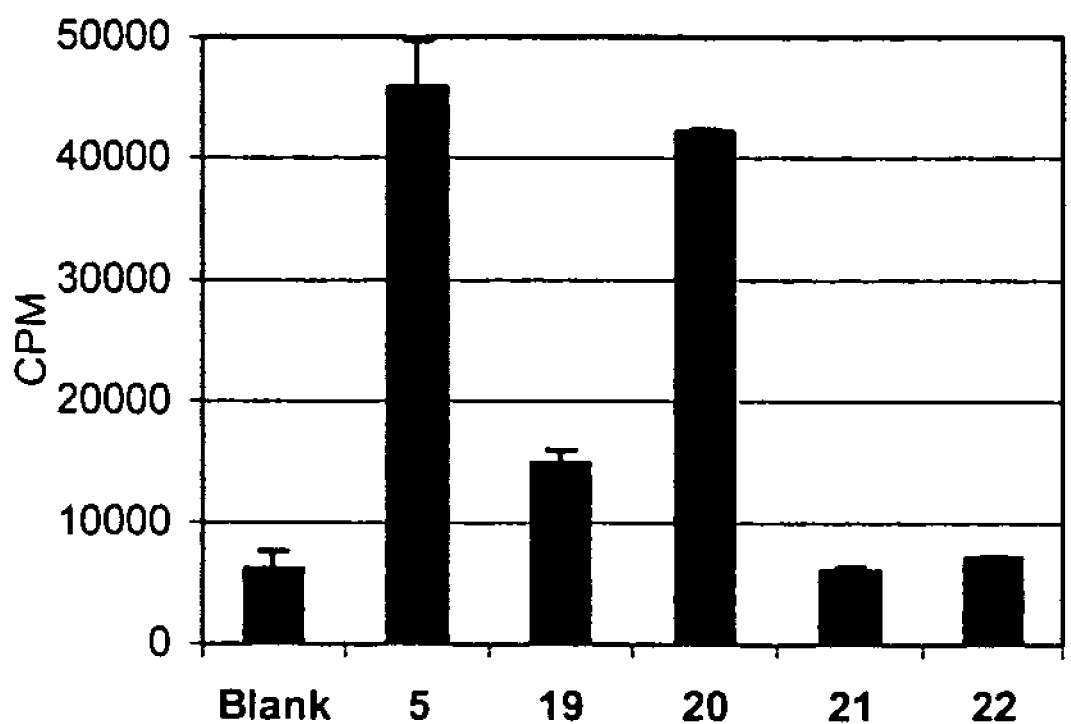
FIG. 13. Comparison of T cell proliferation in the presence of modified peptides 19, 20, 21, and 22. All peptides were tested at a concentration of 3 μM, except compound 22 was tested at 5 μM. DQ2 APCs were γ-irradiated before incubation with peptide.
Figure 14:
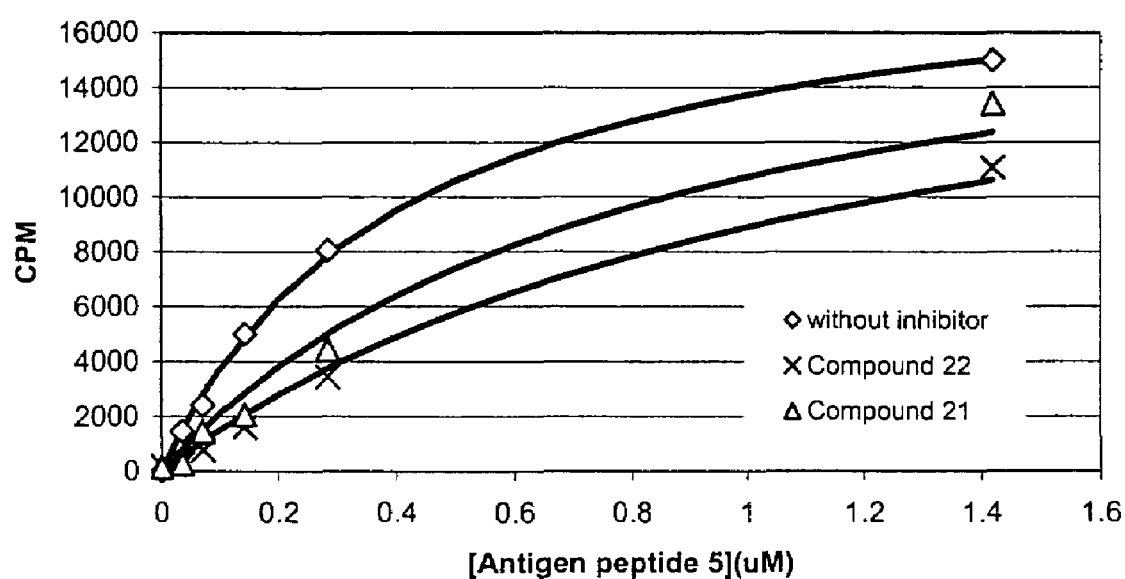
FIG. 14. T cell response to various concentrations of antigen peptide 5 co-incubated without any blocker peptide or in the presence of compound 21 or compound 22 (5 μM each) as reversible inhibitors of DQ2 antigen presentation. DQ2 APCs were fixed prior to incubation with peptide.

Peptide derivatives 17-22 (see FIG. 10) were synthesized with N-α-t-Boc-N-ε-Fmoc-L-lysine. The Fmoc-protected side chain of lysine was deprotected after synthesis of the full-length peptide by washing the resin twice in 20% piperidine in dimethylformamide for 15 min. Then 1 g of succinimide anhydride dissolved in 2 ml dimethylformamide was added to the resin for 30 min. The extent of amide formation was monitored by the ninhydrin test.

The dimeric peptide 22 was synthesized from pure monomeric fluorescein labeled peptide 17. Fluorescein-conjugated 17 was mixed with bis-d PEG 6 NHS ester (Quanta Biodesign) in 2:1 ratio in either dimethylformamide with 10% v/v diisopropylethylamine as base, or in pH 9 phosphate solution. The reaction was monitored by analytical reverse phase HPLC using a $C_{18}$ column. The product peak eluted 2 min after the monomeric starting material, and was purified by preparative reverse phase HPLC. Mass spectrometric analysis revealed that it had the expected molecular weight of 5858.8 (22+$Na^+$, exp. MW 5858). The concentration of this fluorescent dimeric peptide was quantified by using the absorption coefficient factor 160,400 $cm^{-1}M^{-1}$ at 495 nm.

Peptide exchange assay. For peptide exchange experiments, the DQ2 heterodimer purified as described above was incubated with fluorescein-conjugated ligands in a 25:1 ratio (i.e. 4.7 μM DQ2 with 0.18 μM fluorescent peptide). Incubations were performed at 37° C. in a 1:1 mixture of PBS buffer (10 mM Pi, 150 mM NaCl, pH 7.3, supplemented with 0.02% $NaN_3$) and McIlvaine's citrate-phosphate buffers (pH 5 or pH 7) such that the final pH was either 5.5 or 7.3, respectively. Peptide binding was measured by high performance size exclusion chromatography (HPSEC) (17). 1 μl of reaction mixture was diluted into 14 μl PBS. 12.5 μl of the diluted material was injected onto a BioSeptember 3000 size exclusion column (Phenomenex), and eluted with PBS buffer at 1 ml/min. The DQ2-peptide complex eluted at 8.5 min, with free peptides emerging ~2 min later. The fluorescence signal was recorded using an in-line Shimadzu RA35 fluorescent detector with excitation wavelength set at 495 nm and emission detection set at 520 nm. Peak areas corresponding to the DQ2-peptide complex and the free peptide were used to calculate the fractional yield of the DQ2-fluoresceinated peptide complex.

Peptide dissociation assay. For dissociation experiments, DQ2-fluoresceinated peptide complexes were prepared by incubating thrombin treated DQ2 (3-5 μM) with 20-fold excess fluorescein-conjugated peptides at pH 5.5 for 25 hours. The buffer composition was a 1:1 mixture of 10 mM PBS buffer and pH 5.1 McIlvaine's citrate-phosphate buffer (24), such that the final pH was 5.5. Excess free peptide was separated from the complex on a chilled spin column (Bio-Rad) packed with Sephadex G50 superfine medium and blocked with 1% BSA solution to minimize the binding of DQ2 to the column. Spin columns were pre-washed with pH 7.3 PBS buffer, and the fluorescein-conjugated peptide+DQ2 mixture was applied to the column. The DQ2-fluoresceinated peptide complex was eluted in a volume of ~230 μl in pH 7.3 PBS buffer. Typically, this DQ2-peptide fraction contained <10% of free peptide. The solution was immediately adjusted to pH 5.5 or pH 7.3, and 20 μM of a tight DQ2 binding peptide (SEQ ID NO:57) (AAIAAVKEEAF) was added to prevent the re-binding of dissociated fluorescent peptide to DQ2. Kinetic measurements of ligand dissociation were performed at 37° C., and a time course was obtained by injecting 20 μl aliquots into HPSEC column.

T cell proliferation assays. The DQ2 homozygous B-lymphoma cell line (LCL) VAVY cells were irradiated with 12,000 rads of γ-irradiation or fixed with 1% paraformaldehyde for 10 minutes as indicated, and incubated with the appropriate peptides overnight in media containing 10% fetal bovine serum, 2% human serum, penicillin and streptomycin at a cell density of $2\times10^6$ cells/ml in 96-well plates. The next day, the volume was doubled to yield a cell density of $1\times10^6$ cells/ml, 50 μl of which was placed into a U-bottom 96-well plate. An equal volume of T-cells (50 μl of $1\times10^6$ cells/ml) was added to each well, and cells were incubated at 37° C. and 5% $CO_2$ for 48 h, at which point 0.5 μCi/well of [methyl-$^3$H] thymidine (Amersham, TRK120) was added. Cells were incubated for an additional 12-14 h and then frozen. After thawing, incorporated thymidine was collected on a filter mat (Wallac, 1205-401) using a Tomtec cell harvester, and counted using a Wallac 1205 Betaplate liquid scintillation counter.

Results

SAR analysis of the binding of the 33-mer peptide to HLA-DQ2. Earlier studies have demonstrated that the highly immunogenic 33-mer peptide from α2-gliadin, (SEQ ID NO:12) LQLQPFPQPELPYPQPELPYPQPELPYPQPQPF, potently displaces pre-bound ligands from the DQ2 binding pocket and also has a long dissociation half-life. These features, together with its natural proteolytic resistance, make this 33-mer peptide an attractive target for engineering an HLA-DQ2 blocking agent. To dissect its structure-activity relationships (SAR), several analogues were synthesized and initially evaluated in peptide exchange assays over a period of 45 h (FIG. 1). Although the percentage of bound peptide is only reported at the 45 h end-point (i.e. at equilibrium), the half-maximum binding times for several of these peptides were obtained, and found to be similar. Therefore, the equilibrium occupancy is representative of DQ2 avidity.

Several noteworthy observations emerge from the data summarized in FIG. 8. First, consistent with earlier data, it is evident that the $\alpha$II epitope (SEQ ID NO:18) (PQPELPYPQ) is the primary binding site in the 33-mer peptide 1. For example, the minimal $\alpha$II epitope bearing peptide 3, has a binding maximum of 7% at pH 5.5, whereas the minimal $\alpha$I epitope bearing peptide 2 saturates at less than 1% at pH 5.5 and is undetectable at pH 7.3. Second, comparison of the DQ2 binding properties of the minimal $\alpha$II epitope 3 with longer analogues (e.g. 6 and 7) reveals that binding efficiency increases as a greater proportion of the 33-mer sequence is included at the C-terminal side of the epitope. Similarly, comparison of the binding properties of the minimal peptide 3 with the N-terminally elongated peptide 4 suggests that the N-terminus of the 33-mer contributes significantly to its DQ2 binding potency. Together, these findings argue that structural determinants on both sides of the core $\alpha$II epitope sequence of the 33-mer influence its immunological characteristics. The importance of flanking sequences is also reinforced when one compares 21-mer peptide 7 with analogues that are incrementally extended on both sides (8, 9, 10 and 1). Interestingly, the difference between peptides 7 and 8 is more pronounced at pH 7 than at pH 5.

The 33-mer peptide 1 contains three Glu residues corresponding to three transglutaminase-catalyzed deamidation sites. To investigate the role of multiple deamidation sites, we synthesized and tested all possible deamidation analogues of the 33-mer (peptides 11-16). Q10E (11) has higher affinity for DQ2 than either Q17E (12) or Q24E (13) at both pH 5 and pH 7, arguing that DQ2 binding of the 33-mer is primarily centered at the N-terminal $\alpha$II epitope, although the other $\alpha$II epitopes can also bind effectively in the MHC pocket. Notably however, introduction of a second deamidation site (e.g. Q10EQ17E (14) or Q10EQ24E (15)) significantly enhances affinity relative to Q10E (11), suggesting that a second acidic residue C-terminal to the core $\alpha$II epitope is important for the optimal immunological properties of the 33-mer. This is also supported by the observation that the doubly deamidated analogue Q17EQ24E (16) approximates the 33-mer binding characteristics.

Taken together, the above data support that a peptide comprising: (i) the first $\alpha$II epitope of the 33-mer, (ii) the N-terminal sequence, and (iii) adequate C-terminal sequence to include at least one additional deamidation site, would be the shortest 33-mer analogue that could capture the essential DQ2 binding characteristics of the natural product. To test this hypothesis, we synthesized the 20-mer peptide 5, and quantitatively compared its ability to bind DQ2 in peptide exchange and dissociation assays. The results, summarized in FIG. 8, show that peptide 5 is comparable to the 33-mer peptide 1 in all in vitro assays. The immunological relevance of these biochemical findings was verified in T cell proliferation assays using a polyclonal T-cell line that responds to all three $\alpha$ epitopes equally well and a clonal T-cell line that responds to the $\alpha$II epitope exclusively. As shown in FIG. 9A, the T cell stimulatory characteristics of peptides 1 and 5 are very similar, both of which are substantially more potent T cell antigens than the minimal $\alpha$II epitope peptide 3. To verify that the enhanced T cell antigenicity of peptides 1 and 5 is due to superior DQ2 binding affinity rather than the ability of these peptides to stimulate a larger population of $\alpha$-epitope responsive T cells, the experiment was repeated using a clonal T cell line specific for the $\alpha$II epitope. FIG. 2B shows that peptides 1 and 5 again have a comparable T cell stimulatory capacity that exceeds that of peptide 3. Thus, in view of its considerably shorter length, peptide 5 serves as a lead for the design of HLA-DQ2 blocking ligands for treatment of Celiac Sprue.

We synthesized truncated analogues (peptides 2, 3, 6-10) as well as site-directed variants (peptides 11-16) of the 33-mer peptide 1, and tested their ability to displace a pre-existing ligand in the binding pocket of a purified, soluble form of HLA-DQ2 (FIG. 8). Our findings suggest that the $\alpha$II epitope centered at E10 is the most preferred register for 33-mer binding to DQ2. This is presumably due to the higher avidity of the $\alpha$II epitope for DQ2 as compared to $\alpha$I and $\alpha$III epitopes, as well as the fact that the first $\alpha$II epitope in the 33-mer peptide can uniquely leverage secondary interactions between the N-terminal (SEQ ID NO:32) LQLQPF sequence and a yet to be determined binding site on HLA-DQ2. Additionally, a second deamidation site located in the C-terminal sequence also facilitates DQ2 binding of this $\alpha$II epitope. Thus, the 20-mer peptide 5 binds to DQ2 equally well as the 33-mer peptide 1, whereas peptide 6 (which lacks the N-terminal flank) has a considerably lower affinity for DQ2 than peptide 5 (which has this flanking sequence). The good correlation between DQ2 binding and T cell proliferative capacity was also verified by showing that peptide 5 has comparable T cell antigenicity as 1 (FIG. 9).

Surprisingly, both 17 and 18 bound poorly to DQ2 at either pH 5 or pH 7 (FIGS. 11A and 11B). We speculated that this poor affinity may be due to formation of a salt bridge between the Lys residue at positions 11 or 18 and the critical Glu residue at the preceding position. To test this hypothesis, the Lys side chains in both compounds were extended with a succinyl group, yielding peptides 19 and 20 (FIG. 3) with a negative charge at residues 11 and 18, respectively. As shown in FIGS. 11A and 11B, peptides 19 and 20 bound to DQ2 with considerably higher affinity. We therefore also synthesized peptide 21, which possesses the above changes at both positions 11 and 18. Peptide 21 bound comparably well with DQ2 as peptide 5, both in exchange experiments (FIG. 4C) and dissociation experiments.

A number of independent investigations have highlighted the feasibility of greatly enhancing ligand avidity to a biological target by the engineering of multivalent ligands. Therefore, in an attempt to further improve DQ2 affinity, a dimeric ligand (22) was synthesized by crosslinking monomeric L11K via a hexa-ethylene glycol (6-PEG) bifunctional linker through the Lys side chains (FIG. 10). Remarkably, this ligand has considerably improved binding affinity for DQ2 as compared to all gluten peptides evaluated thus far, including the 33-mer peptide 1 (FIG. 12).

Since the modified side-chains of ligands 19-22 are oriented toward the T cell face of the DQ2-peptide complex, we anticipated that these modifications were likely to alter the T cell recognition properties of these peptides. As an initial test of this hypothesis, peptides 5 and 19-21 were labeled with biotin at their N termini and mixed with live VAVY (DQ2 homozygous) antigen presenting cells. The extent to which these peptides were presented on the cell surface was visualized using fluorescent streptavidin. After 24 h, the intensity of staining of the VAVY cell surface was found to be comparable by confocal microscopy in the presence of all labeled peptides.

Next, we wished to investigate the extent to which compounds 19-22 were able to elicit a proliferative response from gluten responsive polyclonal T cell lines derived from small intestinal biopsies of Celiac Sprue patients. For this experiment, a T cell line that is strongly responsive to the 33-mer peptide 1 (or alternately peptide 5) was used. As shown in FIG. 13, peptide 20 elicited the strongest T cell response, presumably because it contained an unmodified all (SEQ ID NO:18)(PQPELPYPQ) epitope. A low but measurable T cell response was also observed for peptides 19 and 22, perhaps because they contained an unmodified αIII (SEQ ID NO:58) (PYPQPELPY) epitope. In contrast, the doubly modified peptide 21, which lacks any of the intact α-gliadin epitopes, completely abrogates T cell recognition. Together, these results suggest that compounds 21 and 22 can be presented on the surface of DQ2 antigen presenting cells, but are relatively unrecognized by gluten specific T cells found in the small intestines of Celiac Sprue patients. Given their intrinsic proteolytic stability, these peptides were therefore evaluated as prototypical DQ2 blocking agents.

To assess the DQ2 blocking properties of the most promising compounds, 21 and 22, paraformaldehyde-fixed VAVY cells were incubated for 12 hours with varying concentrations of antigenic peptide 5 in the presence or absence of 5 μM blocker peptide, and the resulting antigen presenting cells were then mixed with gluten responsive T cells under appropriate culture conditions (FIG. 14). A significant increase in $EC_{50}$ was observed in the presence of compounds 21 and 22, indicating that these synthetic peptides were indeed capable of competitively blocking T cell proliferation by potent gluten antigens such as peptide 5.

Discussion

Several recent reports have highlighted the exceptional pathogenic characteristics of a 33-mer peptide from α2 gliadin, (SEQ ID NO:12) LQLQPF-PQPELPYPQPELPYPQPELPYPQPQPF, using disease specific T cells derived from small intestinal biopsies of Celiac Sprue patients. The goal of this research is to evaluate the feasibility of transforming this potent pro-inflammatory natural product into a fundamentally new type of anti-inflammatory agent for potential use in Celiac Sprue patients. To this end we have dissected the structure-function relationships of the 33-mer peptide, and have harnessed these insights, together with our recent X-ray crystal structure of HLA-DQ2, to design prototypical DQ2 blocking ligands.

The 33-mer peptide is a multivalent antigen possessing at least six overlapping copies of three distinct epitopes (designated earlier as αI, αII and αIII epitopes, corresponding to the sequences (SEQ ID NO:17) PFPQPELPY, (SEQ ID NO:18) PQPELPYPQ and (SEQ ID NO:58) PYPQPELPY, respectively). However, its predominant mode of DQ2 interaction involves formation of stable monomeric complexes (1:1 stoichiometry). Detailed equilibrium binding and kinetic analysis of the 33-mer peptide to HLA-DQ2 led us to hypothesize that this peptide derives its DQ2 avidity through a combination of interactions between one or more core epitopes as well as flanking sequences. Therefore, a first objective of this study was to identify the preferred binding epitope(s), the structural determinants in the flanking sequences, and the precise contributions of the three Glu residues, each of which is generated by post-translational deamidation of a naturally occurring Gln residue by the human transglutaminase 2 enzyme.

We synthesized truncated analogues (peptides 2, 3, 6-10) as well as site-directed variants (peptides 11-16) of the 33-mer peptide 1 (Table 3), and tested their ability to displace a pre-existing ligand in the binding pocket of a purified, soluble form of HLA-DQ2 (FIG. 8). Our findings suggest that the αII epitope centered at E10 is the most preferred register for 33-mer binding to DQ2. This is presumably due to the higher avidity of the αII epitope for DQ2 as compared to αI and αIII epitopes, as well as the fact that the first αII epitope in the 33-mer peptide can uniquely leverage secondary interactions between the N-terminal (SEQ ID NO:32) LQLQPF sequence and a yet to be determined binding site on HLA-DQ2. Additionally, a second deamidation site located in the C-terminal sequence also facilitates DQ2 binding of this αII epitope. Thus, the 20-mer peptide 5 binds to DQ2 equally well as the 33-mer peptide 1, whereas peptide 6 (which lacks the N-terminal flank) has a considerably lower affinity for DQ2 than peptide 5 (which has this flanking sequence). The good correlation between DQ2 binding and T cell proliferative capacity was also verified by showing that peptide 5 has comparable T cell antigenicity as 1 (FIG. 9).

The X-ray crystal structure of HLA-DQ2 bound to the αI gliadin epitope had revealed that some amino acid side chains from the epitope are deeply buried in the DQ2 binding pocket, whereas others face outward, presumably in the direction of the T cell receptor. L11 and L18 in peptide 5 are examples of the latter category of residues, regardless of whether they are recognized by DQ2 as part of an αII epitope (where they bind in the P5 binding pocket) or the αI or αIII epitopes (where they bind in the P7 pocket). Leu->Lys substitutions at these positions therefore provided functional handles for further modification. Several analogues (17-21) of peptide 5 were evaluated; of these, compounds 19, 20, and 21 had similar affinity for HLA-DQ2 as unsubstituted peptide 5 (FIG. 11). In T cell assays, whereas peptides 19 and 20 did retain some ability to stimulate the proliferation of gluten specific T cells from intestinal biopsies of Celiac Sprue patients, the doubly modified peptide 21 is unable to stimulate an αI, αII, and αIII epitope responsive T cell line (FIG. 13). In the presence of 5 μM 21, the $EC_{50}$ of antigenic peptide 5 against gluten specific T cells is increased.

An alternative design of potential DQ2 blocking agents involved dimerization of peptide 17 through the Lys-11 side chain. This strategy has borne fruit in the study of protein-protein interactions in other biological contexts. Our prototypical dimeric peptide 22 with a hexa-ethylene glycol bifunctional linker had a substantially enhanced affinity for HLA-DQ2 than both peptides 1 and 5 at pH 5 or pH 7. Moreover, compound 22 showed remarkably enhanced binding kinetics, reaching half maximal DQ2 occupancy at 2.5 hr instead of ~8 hr for the 33-mer peptide 1 (FIG. 5). This rapid binding capacity could be a pharmacologically useful property in the context of inhibiting antigen presentation. In support of this anti-inflammatory potential, addition of 5 μM compound 22 also resulted in a significant elevation of the $EC_{50}$ of antigenic peptide 5.

In summary, our studies reported here have led to the development of an improved insight into the structure-activity relationships of the highly immunogenic 33-mer peptide from α2-gliadin, and in turn, to the design of peptidic analogues of this peptide that bind tightly to HLA-DQ2 but are not recognized by Celiac Sprue associated T cells. The design of future generations of such DQ2 blocking agents will require in-depth biological evaluations of these promising synthetic agents.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A purified oligopeptide, wherein the oligopeptide comprises SEQ ID NO:33, LQLQPFPQPEKPYPQPELPY.

2. A purified oligopeptide, wherein the oligopeptide comprises SEQ ID NO:35, LQLQPFPQPEKPYPQPEKPY.

3. A purified oligopeptide comprising SEQ ID NO:33, LQLQPFPQPEKPYPQPELPY, or SEQ ID NO:35 LQLQPFPQPEKPYPQPEKPY wherein residues 11 and 18 are modified with cysteine substitutions.

4. The purified oligopeptide of claim 3, wherein the cysteine residues are replaced with homocysteine.

5. A purified oligopeptide selected from the group consisting of SEQ ID NO:35, LQLQPFPQPEKPYPQPEKPY and SEQ ID NO:33, LQLQPFPQPEKPYPQPELPY.

6. The purified oligopeptide of any one of claims 1-5, wherein one or more lysine residues are conjugated to a group that provides for steric hindrance of interactions between the peptide and a cognate receptor.

7. The purified oligopeptide of claim any one of claims 1-5, wherein one or more lysine residues are conjugated to succinic acid; a benzyloxycarbonyl group; a t-Butoxycarbonyl group; a 9- fluorenylmethoxycarbonyl group; a phthalimide; or polyethylene glycol.

* * * * *

UNITED STATES PATENT AND TRADEMARK OFFICE
CERTIFICATE OF CORRECTION

PATENT NO. : 7,462,688 B2
APPLICATION NO. : 11/198068
DATED : December 9, 2008
INVENTOR(S) : Chaitan Khosla et al.

It is certified that error appears in the above-identified patent and that said Letters Patent is hereby corrected as shown below:

In The Specification:

- Column 34, lines 23-43: Please replace paragraph [155] with the following rewritten paragraph:

--*Design and in vitro evaluation of DQ2 blocking peptides.* A major goal of this research is to design and characterize medicinally appropriate ligands that form tight, long-lived complexes with HLA-DQ2 on the surface of antigen presenting cells in the Celiac small intestine, but are not recognized by disease specific T cells. Toward this end we synthesized analogues of the 20-mer peptide 5, and evaluated their DQ2 binding properties. Our initial design targeted L11 and L18 residues of peptide 5 as modification sites. L11 was chosen based on the crystal structure of the αI-DQ2 complex, which suggested that the residue at the corresponding position (i.e. the P5 Pro residue) points away from the DQ2 protein surface. Consistent with this observation, epitope scanning experiments have also shown that the antigen binding pocket of DQ2 can accommodate a spectrum of amino acids at the P5 position. Therefore, the L11K analogue (17) shown in Figure 10 was synthesized. In addition, since peptide 5 can bind to HLA-DQ2 in the αI (SEQ ID NO:17) (PFPQPELPY) and αII (SEQ ID NO:18) (PQPELPYPQ) epitope registers, we also wished to introduce modifications in the downstream αIII epitope. For this reason L18K (18) was also synthesized. (Like the P5 residue, the P7 residue also points away from the DQ2 protein surface.)--

Figure 8:
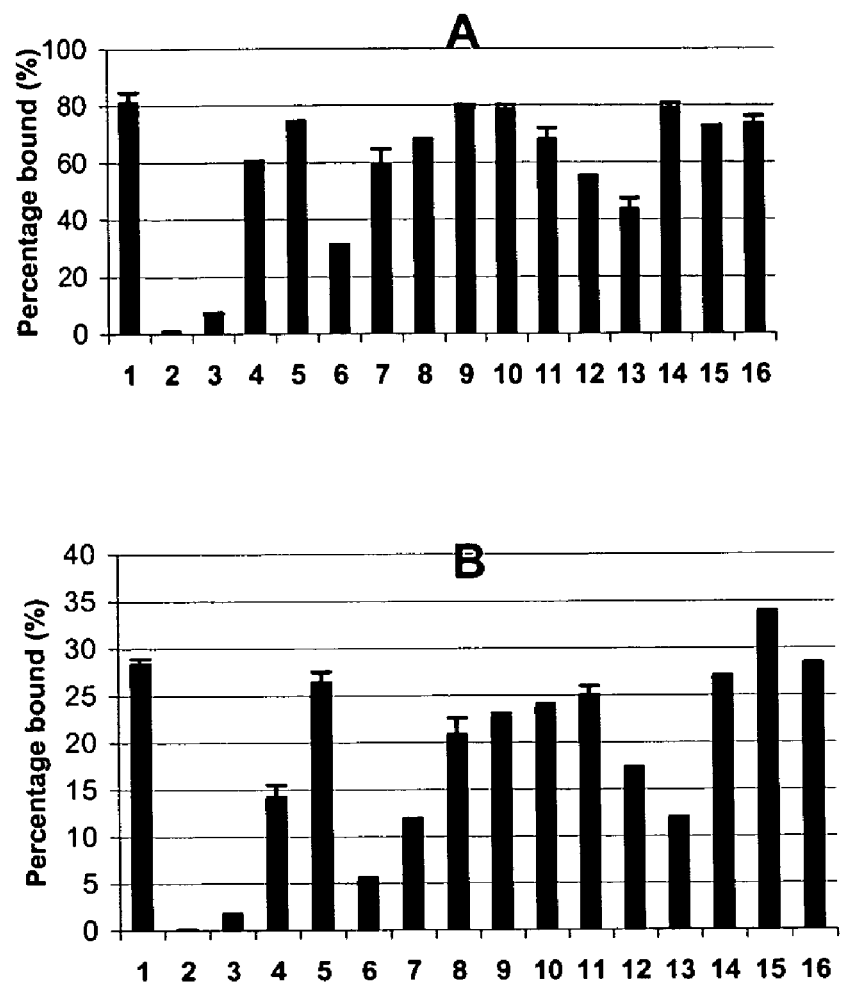
FIG. 8. Equilibrium occupancy of individual peptides shown in FIG. 10 in the DQ2 binding pocket, as measured by peptide exchange assays. Measurements were made at (A) pH 5.5 and (B) pH 7.3. 4.7 µM DQ2 was mixed with 0.18 µM fluorescein-conjugated peptide at 37° C. for 45 h, and the abundance of DQ2 bound peptide was calculated as a percentage of total peptide.

- Column 36, lines 10-30: Please replace paragraph [163] with the following rewritten paragraph:

--We synthesized truncated analogues (peptides 2, 3, 6-10) as well as site-directed variants (peptides 11-16) of the 33-mer peptide 1, and tested their ability to displace a pre-existing ligand in the binding pocket of a purified, soluble form of HLA-DQ2 (FIG. 8). Our findings suggest that the αII epitope centered at E10 is the most preferred register for 33-mer binding to DQ2. This is presumably due to the higher avidity of the αII epitope for DQ2 as compared to αI and αIII epitopes, as well as the fact that the first αII epitope in the 33-mer peptide can uniquely leverage secondary interactions between the N-terminal (SEQ ID NO:32) LQLQPF sequence and a yet to be determined binding site on HLA-DQ2. Additionally, a second deamidation site located in the C-terminal sequence also facilitates DQ2 binding of this αII epitope. Thus, the 20-mer peptide 5 binds to DQ2 equally well as the 33-mer peptide 1, whereas peptide 6 (which lacks the N-terminal flank) has a considerably lower

Figure 9:
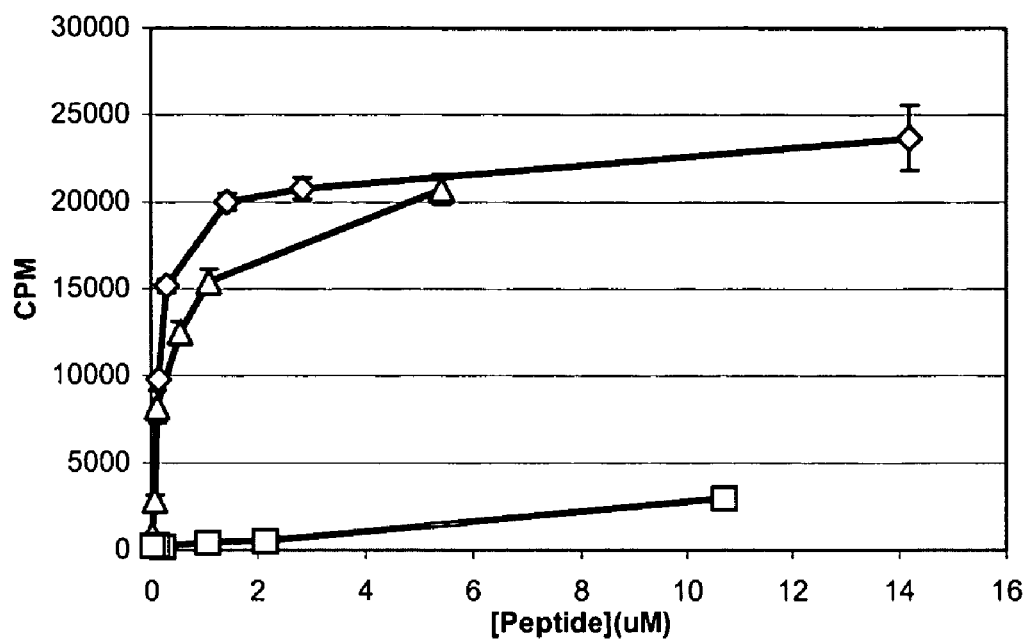
FIG. 9A-9B. Stimulation of T cell proliferation by three peptides, the 33-mer 1 (Δ), peptide 3 ( ), and the 20-mer 5 (◊). Paraformaldehyde-fixed DQ2 cells were used as antigen presenting cells. (A) Proliferation of a polyclonal T cell line that recognizes all α epitopes. (B) Proliferation of a clonal T cell line that recognizes the αII epitope (peptide 3).
Figure 9:
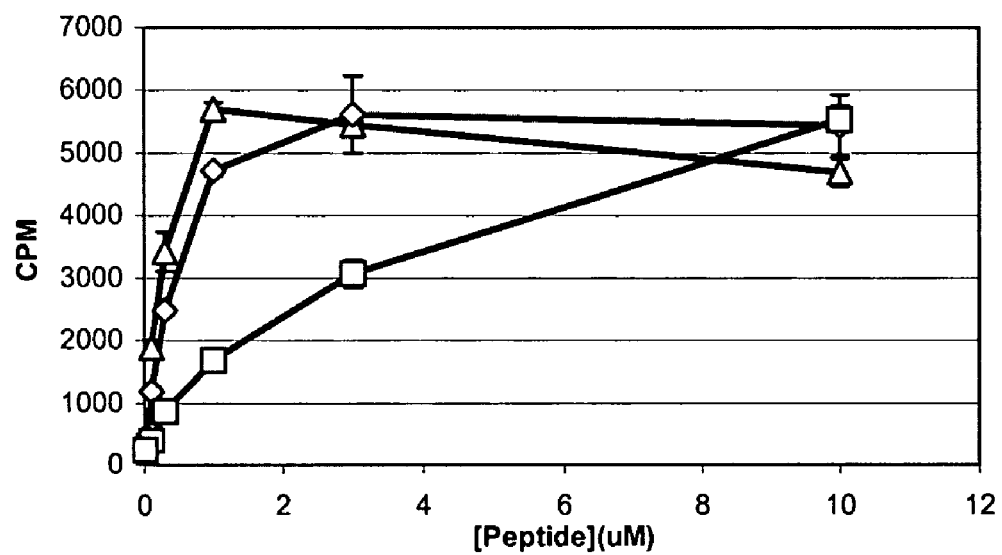

CERTIFICATE OF CORRECTION (continued)
U.S. Pat. No. 7,462,688 B2 affinity for DQ2 than peptide 5 (which has this flanking sequence). The good correlation between DQ2 binding and T cell proliferative capacity was also verified by showing that peptide 5 has comparable T cell antigenicity as 1 (FIG. 9).--

Signed and Sealed this

Nineteenth Day of January, 2010

David J. Kappos
*Director of the United States Patent and Trademark Office*

```
                              SEQUENCE LISTING

<160> NUMBER OF SEQ ID NOS: 58

<210> SEQ ID NO 1
<211> LENGTH: 12
<212> TYPE: PRT
<213> ORGANISM: Triticum aestivum

<400> SEQUENCE: 1

Gln Leu Gln Pro Phe Pro Gln Pro Gln Leu Pro Tyr
 1               5                   10

<210> SEQ ID NO 2
<211> LENGTH: 12
<212> TYPE: PRT
<213> ORGANISM: Triticum aestivum
<220> FEATURE:
<221> NAME/KEY: PYRROLIDONE CARBOXYLIC ACID
<222> LOCATION: (1)...(1)
<223> OTHER INFORMATION: N terminal pyroglutaminate

<400> SEQUENCE: 2

Gln Leu Gln Pro Phe Pro Gln Pro Gln Leu Pro Tyr
 1               5                   10

<210> SEQ ID NO 3
<211> LENGTH: 14
<212> TYPE: PRT
<213> ORGANISM: Triticum aestivum

<400> SEQUENCE: 3

Pro Gln Pro Gln Leu Pro Tyr Pro Gln Pro Gln Leu Pro Tyr
 1               5                   10

<210> SEQ ID NO 4
<211> LENGTH: 13
<212> TYPE: PRT
<213> ORGANISM: Triticum aestivum

<400> SEQUENCE: 4

Pro Gln Pro Gln Leu Pro Tyr Pro Gln Pro Gln Leu Pro
 1               5                   10

<210> SEQ ID NO 5
<211> LENGTH: 11
<212> TYPE: PRT
<213> ORGANISM: Triticum aestivum

<400> SEQUENCE: 5

Gln Leu Gln Pro Phe Pro Gln Pro Gln Leu Pro
 1               5                   10
```

```
<210> SEQ ID NO 6
<211> LENGTH: 11
<212> TYPE: PRT
<213> ORGANISM: Triticum aestivum

<400> SEQUENCE: 6

Gln Pro Gln Phe Pro Gln Pro Gln Leu Pro Tyr
1               5                   10

<210> SEQ ID NO 7
<211> LENGTH: 9
<212> TYPE: PRT
<213> ORGANISM: Triticum aestivum

<400> SEQUENCE: 7

Gln Pro Phe Pro Gln Pro Gln Leu Pro
1               5

<210> SEQ ID NO 8
<211> LENGTH: 6
<212> TYPE: PRT
<213> ORGANISM: Triticum aestivum

<400> SEQUENCE: 8

Pro Gln Pro Gln Leu Pro
1               5

<210> SEQ ID NO 9
<211> LENGTH: 13
<212> TYPE: PRT
<213> ORGANISM: Triticum aestivum

<400> SEQUENCE: 9

Arg Arg Leu Ile Glu Asp Asn Glu Tyr Thr Ala Arg Gly
1               5                   10

<210> SEQ ID NO 10
<211> LENGTH: 8
<212> TYPE: PRT
<213> ORGANISM: Triticum aestivum

<400> SEQUENCE: 10

Trp Gln Ile Pro Glu Gln Ser Arg
1               5

<210> SEQ ID NO 11
<211> LENGTH: 7
<212> TYPE: PRT
<213> ORGANISM: Triticum aestivum

<400> SEQUENCE: 11

Phe Pro Gln Pro Gln Leu Pro
1               5

<210> SEQ ID NO 12
<211> LENGTH: 33
<212> TYPE: PRT
<213> ORGANISM: Triticum aestivum

<400> SEQUENCE: 12

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30
```

Phe

<210> SEQ ID NO 13
<211> LENGTH: 34
<212> TYPE: PRT
<213> ORGANISM: Triticum aestivum

<400> SEQUENCE: 13

Gln Pro Gln Pro Phe Pro Pro Gln Leu Pro Tyr Pro Gln Thr Gln Pro
1               5                   10                  15

Phe Pro Pro Gln Gln Pro Tyr Pro Gln Pro Gln Pro Tyr Pro Gln
            20                  25                  30

Pro Gln

<210> SEQ ID NO 14
<211> LENGTH: 35
<212> TYPE: PRT
<213> ORGANISM: Triticum aestivum

<400> SEQUENCE: 14

Gln Gln Gln Pro Phe Pro Gln Gln Pro Ile Pro Gln Gln Pro Gln Pro
1               5                   10                  15

Tyr Pro Gln Gln Pro Gln Pro Tyr Pro Gln Gln Pro Phe Pro Pro Gln
            20                  25                  30

Gln Pro Phe
        35

<210> SEQ ID NO 15
<211> LENGTH: 30
<212> TYPE: PRT
<213> ORGANISM: Triticum aestivum

<400> SEQUENCE: 15

Gln Pro Phe Pro Gln Pro Gln Gln Thr Phe Pro Gln Gln Pro Gln Leu
1               5                   10                  15

Pro Phe Pro Gln Gln Pro Gln Gln Pro Phe Pro Gln Pro Gln
            20                  25                  30

<210> SEQ ID NO 16
<211> LENGTH: 30
<212> TYPE: PRT
<213> ORGANISM: Triticum aestivum

<400> SEQUENCE: 16

Gln Pro Phe Pro Gln Pro Gln Gln Pro Thr Pro Ile Gln Pro Gln Gln
1               5                   10                  15

Pro Phe Pro Gln Arg Pro Gln Gln Pro Phe Pro Gln Pro Gln
            20                  25                  30

<210> SEQ ID NO 17
<211> LENGTH: 9
<212> TYPE: PRT
<213> ORGANISM: Triticum aestivum

<400> SEQUENCE: 17

Pro Phe Pro Gln Pro Glu Leu Pro Tyr
1               5

<210> SEQ ID NO 18
<211> LENGTH: 9
<212> TYPE: PRT

-continued

<213> ORGANISM: Triticum aestivum

<400> SEQUENCE: 18

Pro Gln Pro Glu Leu Pro Tyr Pro Gln
1               5

<210> SEQ ID NO 19
<211> LENGTH: 15
<212> TYPE: PRT
<213> ORGANISM: Triticum aestivum

<400> SEQUENCE: 19

Leu Gln Leu Gln Pro Phe Pro Gln Pro Glu Leu Pro Tyr Pro Gln
1               5                   10                  15

<210> SEQ ID NO 20
<211> LENGTH: 20
<212> TYPE: PRT
<213> ORGANISM: Triticum aestivum

<400> SEQUENCE: 20

Leu Gln Leu Gln Pro Phe Pro Gln Pro Glu Leu Pro Tyr Pro Gln Pro
1               5                   10                  15

Glu Leu Pro Tyr
            20

<210> SEQ ID NO 21
<211> LENGTH: 14
<212> TYPE: PRT
<213> ORGANISM: Triticum aestivum

<400> SEQUENCE: 21

Pro Gln Pro Glu Leu Pro Tyr Pro Gln Pro Glu Leu Pro Tyr
1               5                   10

<210> SEQ ID NO 22
<211> LENGTH: 21
<212> TYPE: PRT
<213> ORGANISM: Triticum aestivum

<400> SEQUENCE: 22

Pro Gln Pro Glu Leu Pro Tyr Pro Gln Pro Glu Leu Pro Tyr Pro Gln
1               5                   10                  15

Pro Glu Leu Pro Tyr
            20

<210> SEQ ID NO 23
<211> LENGTH: 28
<212> TYPE: PRT
<213> ORGANISM: Triticum aestivum

<400> SEQUENCE: 23

Pro Phe Pro Gln Pro Glu Leu Pro Tyr Pro Gln Pro Glu Leu Pro Tyr
1               5                   10                  15

Pro Gln Pro Glu Leu Pro Tyr Pro Gln Pro Gln Pro
            20                  25

<210> SEQ ID NO 24
<211> LENGTH: 30
<212> TYPE: PRT
<213> ORGANISM: Triticum aestivum

<400> SEQUENCE: 24

```
Leu Gln Pro Phe Pro Gln Pro Glu Leu Pro Tyr Pro Gln Glu Leu
1               5                   10                  15

Pro Tyr Pro Gln Pro Glu Leu Pro Tyr Pro Gln Pro
            20                  25                  30
```

<210> SEQ ID NO 25
<211> LENGTH: 31
<212> TYPE: PRT
<213> ORGANISM: Triticum aestivum

<400> SEQUENCE: 25

```
Gln Leu Gln Pro Phe Pro Gln Pro Glu Leu Pro Tyr Pro Gln Pro Glu
1               5                   10                  15

Leu Pro Tyr Pro Gln Pro Glu Leu Pro Tyr Pro Gln Pro
            20                  25                  30
```

<210> SEQ ID NO 26
<211> LENGTH: 33
<212> TYPE: PRT
<213> ORGANISM: Triticum aestivum

<400> SEQUENCE: 26

```
Leu Gln Leu Gln Pro Phe Pro Gln Pro Glu Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe
```

<210> SEQ ID NO 27
<211> LENGTH: 33
<212> TYPE: PRT
<213> ORGANISM: Triticum aestivum

<400> SEQUENCE: 27

```
Leu Gln Leu Gln Pro Phe Pro Gln Pro Gln Leu Pro Tyr Pro Gln Pro
1               5                   10                  15

Glu Leu Pro Tyr Pro Gln Pro Gln Leu Pro Tyr Pro Gln Pro Gln Pro
            20                  25                  30

Phe
```

<210> SEQ ID NO 28
<211> LENGTH: 33
<212> TYPE: PRT
<213> ORGANISM: Triticum aestivum

<400> SEQUENCE: 28

```
Leu Gln Leu Gln Pro Phe Pro Gln Pro Gln Leu Pro Tyr Pro Gln Pro
1               5                   10                  15

Gln Leu Pro Tyr Pro Gln Pro Glu Leu Pro Tyr Pro Gln Pro Gln Pro
            20                  25                  30

Phe
```

<210> SEQ ID NO 29
<211> LENGTH: 33
<212> TYPE: PRT
<213> ORGANISM: Triticum aestivum

<400> SEQUENCE: 29

```
Leu Gln Leu Gln Pro Phe Pro Gln Pro Glu Leu Pro Tyr Pro Gln Pro
1               5                   10                  15
```

Glu Leu Pro Tyr Pro Gln Pro Gln Leu Pro Tyr Pro Gln Pro
        20                        25                   30

Phe

<210> SEQ ID NO 30
<211> LENGTH: 33
<212> TYPE: PRT
<213> ORGANISM: Triticum aestivum

<400> SEQUENCE: 30

Leu Gln Leu Gln Pro Phe Pro Gln Pro Glu Leu Pro Tyr Pro Gln Pro
1               5                   10                  15

Gln Leu Pro Tyr Pro Gln Pro Glu Leu Pro Tyr Pro Gln Pro
        20                      25                   30

Phe

<210> SEQ ID NO 31
<211> LENGTH: 33
<212> TYPE: PRT
<213> ORGANISM: Triticum aestivum

<400> SEQUENCE: 31

Leu Gln Leu Gln Pro Phe Pro Gln Pro Gln Leu Pro Tyr Pro Gln Pro
1               5                   10                  15

Glu Leu Pro Tyr Pro Gln Pro Glu Leu Pro Tyr Pro Gln Pro
        20                      25                   30

Phe

<210> SEQ ID NO 32
<211> LENGTH: 6
<212> TYPE: PRT
<213> ORGANISM: Triticum aestivum

<400> SEQUENCE: 32

Leu Gln Leu Gln Pro Phe
1               5

<210> SEQ ID NO 33
<211> LENGTH: 20
<212> TYPE: PRT
<213> ORGANISM: Triticum aestivum

<400> SEQUENCE: 33

Leu Gln Leu Gln Pro Phe Pro Gln Pro Glu Lys Pro Tyr Pro Gln Pro
1               5                   10                  15

Glu Leu Pro Tyr
        20

<210> SEQ ID NO 34
<211> LENGTH: 20
<212> TYPE: PRT
<213> ORGANISM: Triticum aestivum

<400> SEQUENCE: 34

Leu Gln Leu Gln Pro Phe Pro Gln Pro Glu Leu Pro Tyr Pro Gln Pro
1               5                   10                  15

Glu Lys Pro Tyr
        20

<210> SEQ ID NO 35
<211> LENGTH: 20

```
<212> TYPE: PRT
<213> ORGANISM: Triticum aestivum

<400> SEQUENCE: 35

Leu Gln Leu Gln Pro Phe Pro Gln Pro Glu Lys Pro Tyr Pro Gln Pro
 1               5                  10                  15

Glu Lys Pro Tyr
            20

<210> SEQ ID NO 36
<211> LENGTH: 7
<212> TYPE: PRT
<213> ORGANISM: Triticum aestivum

<400> SEQUENCE: 36

Pro Gln Pro Glu Leu Pro Tyr
 1               5

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43
<211> LENGTH: 9
<212> TYPE: PRT
<213> ORGANISM: Triticum aestivum

<400> SEQUENCE: 43

Pro Gln Pro Glu Lys Pro Tyr Pro Gln
 1               5

<210> SEQ ID NO 44
<211> LENGTH: 5
<212> TYPE: PRT
```

-continued

<213> ORGANISM: Triticum aestivum

<400> SEQUENCE: 44

Pro Glu Leu Pro Tyr
1               5

<210> SEQ ID NO 45
<211> LENGTH: 5
<212> TYPE: PRT
<213> ORGANISM: Triticum aestivum

<400> SEQUENCE: 45

Pro Glu Lys Pro Tyr
1               5

<210> SEQ ID NO 46
<211> LENGTH: 10
<212> TYPE: PRT
<213> ORGANISM: Triticum aestivum

<400> SEQUENCE: 46

Pro Phe Pro Gln Pro Glu Leu Pro Tyr Pro
1               5                   10

<210> SEQ ID NO 47
<211> LENGTH: 13
<212> TYPE: PRT
<213> ORGANISM: Triticum aestivum

<400> SEQUENCE: 47

Pro Gln Pro Glu Leu Pro Tyr Pro Gln Pro Gln Leu Pro
1               5                   10

<210> SEQ ID NO 48
<211> LENGTH: 11
<212> TYPE: PRT
<213> ORGANISM: Triticum aestivum

<400> SEQUENCE: 48

Pro Gln Gln Ser Phe Pro Glu Gln Gln Pro Pro
1               5                   10

<210> SEQ ID NO 49
<211> LENGTH: 14
<212> TYPE: PRT
<213> ORGANISM: Triticum aestivum

<400> SEQUENCE: 49

Val Gln Gly Gln Gly Ile Ile Gln Pro Glu Gln Pro Ala Gln
1               5                   10

<210> SEQ ID NO 50
<211> LENGTH: 13
<212> TYPE: PRT
<213> ORGANISM: Triticum aestivum

<400> SEQUENCE: 50

Phe Pro Glu Gln Pro Gln Gln Pro Tyr Pro Gln Gln Pro
1               5                   10

<210> SEQ ID NO 51
<211> LENGTH: 13
<212> TYPE: PRT
<213> ORGANISM: Triticum aestivum

```
<400> SEQUENCE: 51

Phe Pro Gln Gln Pro Glu Gln Pro Tyr Pro Gln Gln Pro
1               5                   10

<210> SEQ ID NO 52
<211> LENGTH: 12
<212> TYPE: PRT
<213> ORGANISM: Triticum aestivum

<400> SEQUENCE: 52

Phe Ser Gln Pro Glu Gln Glu Phe Pro Gln Pro Gln
1               5                   10

<210> SEQ ID NO 53
<211> LENGTH: 7
<212> TYPE: PRT
<213> ORGANISM: Triticum aestivum

<400> SEQUENCE: 53

Pro Gln Pro Gln Leu Pro Tyr
1               5

<210> SEQ ID NO 54
<211> LENGTH: 9
<212> TYPE: PRT
<213> ORGANISM: Triticum aestivum

<400> SEQUENCE: 54

Pro Tyr Pro Gln Pro Glu Leu Pro Tyr
1               5

<210> SEQ ID NO 55
<211> LENGTH: 12
<212> TYPE: PRT
<213> ORGANISM: Triticum aestivum

<400> SEQUENCE: 55

Gln Leu Gln Pro Phe Pro Gln Pro Glu Leu Pro Tyr
1               5                   10

<210> SEQ ID NO 56
<211> LENGTH: 15
<212> TYPE: PRT
<213> ORGANISM: Triticum aestivum

<400> SEQUENCE: 56

Gly Ala Gly Ser Leu Val Pro Arg Gly Ser Gly Gly Gly Gly Ser
1               5                   10                  15

<210> SEQ ID NO 57
<211> LENGTH: 11
<212> TYPE: PRT
<213> ORGANISM: Triticum aestivum

<400> SEQUENCE: 57

Ala Ala Ile Ala Ala Val Lys Glu Glu Ala Phe
1               5                   10

<210> SEQ ID NO 58
<211> LENGTH: 9
<212> TYPE: PRT
<213> ORGANISM: Triticum aestivum

<400> SEQUENCE: 58
```

-continued

```
Pro Tyr Pro Gln Pro Glu Leu Pro Tyr
1               5
```